US010731216B2

(12) United States Patent
Ceccatelli et al.

(10) Patent No.: US 10,731,216 B2
(45) Date of Patent: Aug. 4, 2020

(54) METHODS AND COMPOSITIONS FOR BIOMARKERS OF DEPRESSION AND PHARMACORESPONSE

(71) Applicants: Sandra Ceccatelli, Stockholm (SE); Dan Stefan Spulber, Segeltorp (SE)

(72) Inventors: Sandra Ceccatelli, Stockholm (SE); Dan Stefan Spulber, Segeltorp (SE)

(73) Assignee: NORTHERNLIGHT DIAGNOSTICS AB, Solna (SE)

( * ) Notice: Subject to any disclaimer, the term of this patent is extended or adjusted under 35 U.S.C. 154(b) by 4 days.

(21) Appl. No.: 15/509,669

(22) PCT Filed: Sep. 9, 2015

(86) PCT No.: PCT/EP2015/070644
§ 371 (c)(1),
(2) Date: Mar. 8, 2017

(87) PCT Pub. No.: WO2016/038107
PCT Pub. Date: Mar. 17, 2016

(65) Prior Publication Data
US 2018/0230536 A1    Aug. 16, 2018

Related U.S. Application Data

(60) Provisional application No. 62/048,474, filed on Sep. 10, 2014, provisional application No. 62/142,652, filed on Apr. 3, 2015.

(51) Int. Cl.
*C12Q 1/6883* (2018.01)
*G16H 50/20* (2018.01)

(52) U.S. Cl.
CPC ........... *C12Q 1/6883* (2013.01); *G16H 50/20* (2018.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2005/0239110 A1    10/2005  Rokutan et al.

FOREIGN PATENT DOCUMENTS

WO    WO 2008/127524 A2    10/2008

OTHER PUBLICATIONS

Archer et al. Inter-Individual Differences in Habitual Sleep Timing and Entrained Phase of Endogenous Circadian Rhythms of BMAL1, PER2 and PER3 mRNA in Human Leukocytes. 2008. Sleep. vol. 31, No. 5, pp. 608-617 and S1. (Year: 2008).*

International Search Report (PCT/ISA/210) dated Nov. 26, 2015, by the European Patent Office as the International Searching Authority for International Application No. PCT/EP2015/070644.
Written Opinion (PCT/ISA/237) dated Nov. 26, 2015, by the European Patent Office as the International Searching Authority for International Application No. PCT/EP2015/070644.
Albrecht, Urs et al., 2001., "The circadian clock and behavior," *Behavioural Brain Research*, 125, (1-2), pp. 89-91.
Albrecht, Urs, 2013, "Circadian Clocks and Mood-Related Behaviors", In A. Kramer & M. Merrow, eds. *Circadian Clocks, Handbook of Experimental Pharmacology.* Handbook of Experimental Pharmacology. Berlin, Heidelberg: Springer Berlin Heidelberg, pp. 227-239.
Bamne, Mikhil N. et al. "Application of an ex vivo cellular model of circadian variation for bipolar disorder research: a proof of concept study", *Bipolar Disorders*, vol. 15, No. 6, Jun. 20, 2013, pp. 694-700, XP055229074.
Brown, Steven A.. a et al., "The period length of fibroblast circadian gene expression varies widely among human individuals", *PLoS biology*, Oct. 2005, vol. 3, Issue 10, pp. 1813-1818.
Harris, Anjanette et al., 2011. "Glucocorticoids, prenatal stress and the programming of disease" *Hormones and Behavior*, 59(3), pp. 279-289.
Hida, Akiko et al., "In vitro circadian period is associated with circadian/sleep preference", *Scientific Reports*, vol. 3, Jun. 25, 2013, XP055229126.
Hu, Kun et al., "Non-random fluctuations and multi-scale dynamics regulation of human activity", Neuroscience, Sep. 24, 2009,, pp. 1-14.
Kaladchibachi, Sevag A. et al., "Glycogen synthase kinase 3, circadian rhythms, and bipolar disorder: a molecular link in the therapeutic action of lithium", *Journal of Circadian Rhythms*, BioMed Central, London, GB, vol. 5, No. 1, Feb. 12, 2007, pp. 1-12, XP021024957.
Kiessling, Silke et al., "Adrenal glucocorticoids have a key role in circadian resynchronization in a mouse model of jet lag", *The Journal of clinical investigation*, Jul. 2010, 120(7), pp. 2600-2609.
Ko, Caroline H., 2006, "Molecular components of the mammalian circadian clock", *Human Molecular Genetics*, vol. 15, Review Issue No. 2, pp. R271-R277.
Lavebratt, Catharina et al., 2010. "PER2 variation is associated with depression vulnerability", *Am J Med Genet B Neuropsychiatr Genetics*, 153B(2), pp. 570-581.
Leliavski, Alxei et al., "Adrenal Clocks and the Role of Adrenal Hormones in the Regulation of Circadian Physiology", *Journal of Biological Rhythms*, Feb. 2015, 30(1), pp. 20-34.
Lippert, Julian et al., "Altered Dynamics in the Circadian Oscillation of Clock Genes in Dermal Fibroblasts of Patients Suffering from Idiopathic Hypersomnia", PLOS ONE, vol. 9, No. 1, Jan. 14, 2014, pp. 1-9, XP055229068.

(Continued)

*Primary Examiner* — Channing S Mahatan
(74) *Attorney, Agent, or Firm* — Buchanan Ingersoll & Rooney P.C.

(57) ABSTRACT

The present invention relates to a method of diagnosing depression (even at an early stage that may precede clinical symptoms), for determining the pharmacoresponse to antidepressants, for managing treatment of psychiatric disorders, including depression, and for treatment of depression in patients. Further provided is a method for screening antidepressants.

9 Claims, 8 Drawing Sheets
Specification includes a Sequence Listing.

(56) References Cited

OTHER PUBLICATIONS

Maccari, S. et al., "The consequences of early life adversity: neurobiological, behavioural and epigenetic adaptations", *Journal of Neuroendocrinology*, 2014, 26(110), pp. 707-723.

Mairesse, Jerome et al., 2013. "Chronic agomelatine treatment corrects the abnormalities in the circadian rhythm of motor activity and sleep/wake cycle induced by prenatal restraint stress in adult rats", *The International Journal of Neuropsychopharmacology / Official Scientific Journal of the Collegium Internationale Neuropsychopharmacologicum (CINP)*, 16(2), pp. 323-338.

Marrocco, Jordan et al., "The effects of antidepressant treatment in prenatally stressed rats support the glutamatergic hypothesis of stress-related disorders", *The Journal of neuroscience : the official journal of the Society for Neuroscience*, Feb. 5, 2014, 34(6), pp. 2015-2024.

McCarthy, Michael J, et al., "Cellular Circadian Clocks in Mood Disorders", *Journal of Biological Rhythms*, vol. 27, No. 5, Oct. 2012, pp. 339-352, XP009187242.

Pagani, Lucia et al., "The Physiological Period Length of the Human Circadian Clock In Vivo Is Directly Proportional to Period in Human Fibroblasts", *PLOS ONE*, vol. 5, No. 10, Oct. 2010, pp. 1-7, XP055059605.

Partonen, Timo et al., 2007, "Three circadian clock genes Per2, Arntl, and Npas2 contribute to winter depression", *Ann Med*, 39(3), pp. 229-238.

Reddy, Timothy E. et al., "The hypersensitive glucocorticoid response specifically regulates period 1 and expression of circadian genes", *Molecular and cellular biology*, Sep. 2012, 32(18), pp. 3756-3767.

Scott, AJ et al., "Shiftwork as a Risk Factor for Depression: A Pilot Study", *International journal of occupational and environmental health*, Jul. 1997, 3(Supplement 2), pp. S2-S9 (abstract only, 1 page).

Sprouse, Jeffrey et al., "Fluoxetine Modulates the Circadian Biological Clock via Phase Advances of Suprachiasmatic Nucleus Neuronal Firing", *Biological Psychiatry*, Elsevier Science, New York, NY; US, vol. 60, No. 8, Oct. 15, 2006, pp. 896-899, XP005697122.

Spulber S. et al., "Alterations in circadian entrainment precede the onset of depression-like behavior that does not respond to fluoxetine", *Translational Psychiatry*, vol. 5, No. 7, Jul. 14, 2015, p. e603 (pp. 1-10), XP055229184.

Tapia-Osorio, Araceli et al., 2013. "Disruption of circadian rhythms due to chronic constant light leads to depressive and anxiety-like behaviors in the rat", *Behavioural brain research*, 252, pp. 1-9.

Welsh, David K. et al., "Bioluminescence imaging of individual fibroblasts reveals persistent, independently phased circadian rhythms of clock gene expression", *Current biology: CB*, Dec. 29, 2004, 14(24), pp. 2289-2295.

Yang S. et al., "Assessment of circadian function in fibroblasts of patients with bipolar disorder", *Molecular Psychiatry*, vol. 14, No. 2, Feb. 26, 2008, pp. 143-155, XP055229183.

Yoo, Seung-Hee et al., "PERIOD2::LUCIFERASE real-time reporting of circadian dynamics reveals persistent circadian oscillations in mouse peripheral tissues", *Proceedings of the National Academy of Sciences of the United States of America*, Apr. 13, 2004, vol. 101, No. 15, pp. 5339-5346.

\* cited by examiner

Figure 1A
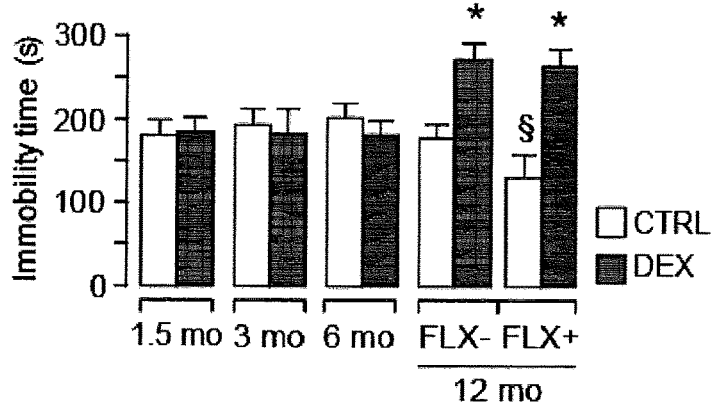
Figure 1B
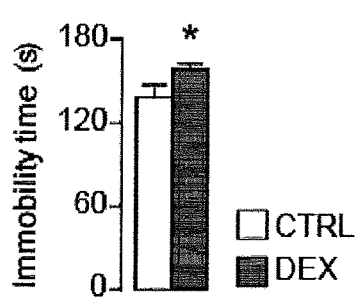
Figure 1C
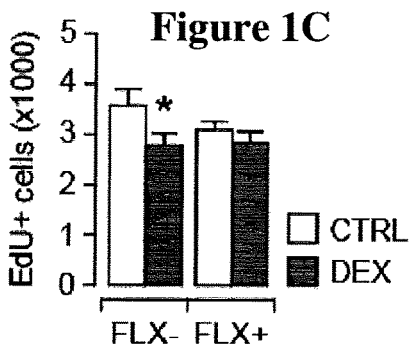
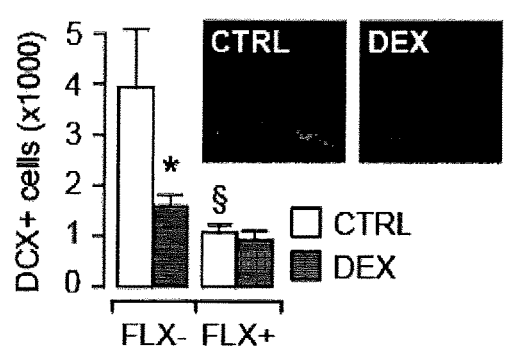
Figure 1D
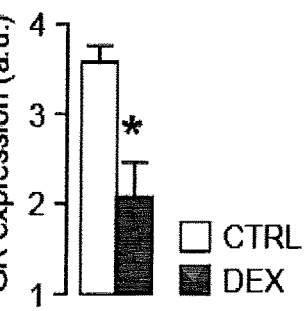
Figure 1E
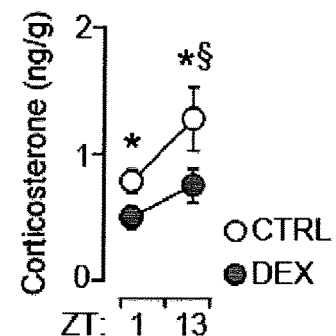
Figure 1F

— normal
— lower amplitude
--- shorter period

— normal
— phase delay
--- phase advance

— normal
— lower amplitude
--- higher amplitude

METHODS AND COMPOSITIONS FOR BIOMARKERS OF DEPRESSION AND PHARMACORESPONSE

FIELD OF THE INVENTION

The present invention relates generally to depression and pharmacoresponse. More specifically the invention relates to a method for early identification of individuals at risk of developing depression and for determining pharmacoresponse to antidepressant treatment.

BACKGROUND OF THE INVENTION

Major Depressive Disorder (MDD)

Major Depression (MD), also referred to as Major Depressive Disorder (MDD), has been recognized by the World Health Organization (WHO) as a major cause of disability. The prevalence has been estimated to about 10% (ranging between 5% in Japan and 16% in the US). Although apparently easy to recognize, MDD is a clinical entity with multiple subtypes (endophenotypes).

Various drug groups with different mechanism of action are available for the treatment of depression. Action mechanisms include, for example, inhibition of serotonin reuptake, inhibition of norepinephrine (noradrenaline) reuptake, inhibition of dopamine reuptake, blockade of presynaptic receptors on serotoninergic neurons and inhibition of an enzyme responsible for degradation of monoamine neurotransmitters. Such a variety of drugs should potentially enable psychiatrists to choose the most beneficial drug or combination of drugs for each individual patient. Still, in everyday clinical practice there is a lack of information about possible symptoms and biomarkers that could characterize patients and that could be used to determine a superior response of one particular class of drug over another.

Selective serotonin reuptake inhibitors (SSRIs) are a class of compounds, which increase the extracellular level of neurotransmitter serotonin by inhibiting its reuptake into the presynaptic neuron. SSRIs are the most frequently prescribed medications for the treatment of MD. However, the efficacy of SSRI treatment in MD is unsatisfactory. It is estimated that approximately one third of patients diagnosed with MD do not achieve or maintain a response to SSRIs.

Currently, antidepressant drugs are administered by a trial and error method. Most commonly prescribed antidepressant medication does not show beneficial effects until about 3 weeks, and the effects reach a maximum after an additional 4-7 weeks. During this time, patients may experience worsening of clinical symptoms and some of them can discontinue the treatment prematurely. As such, to minimise risk and suffering for patients and costs to society it would be valuable to know whether drugs such an antidepressants are likely to be effective before commencing treatment.

Disruption of the Circadian Rhythm is Causative of Neuropsychiatric Disorders

The circadian clock is an internal oscillator identified in all living organisms, which allows the synchronisation of biological function to the light-dark cycle (Ko & Takahashi 2006). In mammals, including humans, this function is performed by a population of neurons located in the hypothalamus, the so-called suprachiasmatic nucleus (SCN). The SCN consists of several neuronal populations that display prominent cyclic fluctuations in firing patterns. The activity of SCN networks synchronises the circadian fluctuations in physiological functions, including hormonal and autonomic regulation of metabolism with the dark-light cycle (see (Leliayski et al. 2014; Kiessling et al. 2010; Albrecht & Oster 2001). The most important input that is able to reset the circadian clock and synchronise it with an externally imposed rhythm is light. Thus, in addition to merely keeping the pace, the SCN function also has a degree of plasticity/adaptability. The regular distribution of activity and resting/sleep periods is an example of output of the circadian clock (Hu et al. 2009). The cyclic expression of clock genes is present and functional in all tissues and cells, for instance, human skin fibroblasts, and can be studied in ex vivo preparations, such as primary cell cultures (Welsh et al. 2004; Brown et al. 2005). Importantly, features of circadian rhythms, while neural in origin, are carried over to cultured fibroblasts in the form of clock genes. At the subcellular level, the core of the molecular clock consists of a network of transcription factors, referred to as the clock genes, engaged in interlocking feedback loops (see review by (Ko & Takahashi 2006). The cyclic function of the clock maintains a large degree of adaptability by integrating information on metabolic status and level of activity with environmental cues (e.g., ambient light intensity) in order to stabilise the 24 h periodicity.

In mammals, for example, humans, shifting or other disruption of the circadian rhythm is causative of or associated with certain pathological states, including among them, jetlag, many neuropsychiatric disorders, such as depression, schizophrenia, ADHD, sleep disorders, such as excessive daytime sleepiness or insomnia and infertility.

The connection between circadian rhythms and major depressive disorder (MDD) is supported by the following lines of evidence:

1) mutations in clock genes are associated with depression (MDD, SAD, as well as sporadic depressive episodes) (Partonen et al. 2007; Lavebratt et al. 2010; Albrecht 2013)
2) tampering with normal circadian rhythms (e.g., shift-work) increases the risk of developing MDD or precipitates the recurrence of MDD episodes (Scott et al. 1997)
3) seasonal affective disorder (SAD) occurs during winter, and is triggered by short light phase during winter months. In animal models, exposure to either continuous darkness or continuous light for extended periods of time leads to depression-like behavior (Tapia-Osorio et al. 2013)
4) therapeutic approaches aimed at restoring/resetting/regulating the circadian rhythms are most often effective in controlling mood. Moreover, treatment with melatonin (a hormone secreted by the pineal gland only during the dark phase, and controlled by direct input from the retina), or agomelatine (a melatonin receptor agonist with established antidepressant effects) are effective mood stabilizers (Mairesse et al. 2013; Marrocco et al. 2014)

A range of factors such as stress, malnutrition and exposure to drugs or chemicals may interfere with critical perinatal developmental periods and have adverse consequences later in life. For example, adverse perinatal events (leading to in utero growth retardation, e.g., from exposure to excess stress hormones) have been shown to increase the risk of metabolic and neuropsychiatric diseases (Harris & Seckl 2011; Maccari et al. 2014). Animal models can be used to study the development, diagnosis and treatment of diseases that have a neurodevelopmental origin, including depression. In addition, pharmacoresponse to a range of drugs can also be studied in such animal models of disease.

Accordingly, there is a need in the art to predict whether drugs, such an antidepressants, are likely to be effective before commencing treatment. There is also a need in the art for agents and methods for diagnosing disorders that are linked with abnormal circadian rhythm.

SUMMARY OF THE INVENTION

The above mentioned problems have now been solved or at least mitigated by the provision of the methods and kits presented herein.

A primary object of the present invention is to provide a method where a subject's alteration in circadian rhythm is used for determining the subject's pharmacoresponse to psychotropic drugs.

Another object of the present invention is to provide a method where a subject's alteration in circadian rhythm is used for determining the patient's pharmacoresponse to antidepressants.

Another object of the present invention is to provide a method where a subject's alteration in circadian rhythm is used for determining the subject's pharmacoresponse to the selective serotonin reuptake inhibitor (SSRI) class of drugs.

Still another object of the present invention is to provide a method where a subject's alteration in circadian rhythm is used for determining the subject's pharmacoresponse to fluoxetine.

Accordingly, there is provided herein a method for identifying alterations in circadian rhythms in a subject that are reflected in changes in the expression of one or more clock gene(s) in said subject, said method comprising: a) obtaining a biological sample from the subject; b) isolating fibroblasts from the sample to provide a second sample; c) synchronising the expression of the clock genes in the second sample by means of a first pulse-exposure of said second sample to a glucocorticoid; d) measuring the expression of clock genes from serial samples from said second sample collected at multiple time points after synchronisation; e) analysing a circadian rhythm parameter(s) (period, amplitude and/or phase) in the series of samples of step (d) and comparing the parameters obtained with circadian rhythm parameters obtained from a control sample to determine a change in the expression of one or more clock gene(s).

There is also provided a method comprising the following steps: a) obtaining a biological sample from the subject; b) isolating fibroblasts from the sample to provide a second sample; c) synchronising the expression of the clock genes in the second sample by means of a first pulse exposure of said second sample to a glucocorticoid; d) measuring the expression of clock genes from serial samples from said second sample collected at multiple time points after synchronisation; e) analysing a circadian rhythm parameter(s) (period, amplitude and/or phase) in the series of samples of step (d), comparing the parameters obtained with circadian rhythm parameters obtained from a control sample to determine a change in the expression of one or more clock gene(s); f) culturing the second sample for a period of time; g) resetting (phaseshifting) the expression of the clock genes with a second pulse-exposure of said second sample to a glucocorticoid; h) measuring the expression of the same clock genes measured in step (d), in serial samples from said second sample collected at multiple time points; and i) analysing a circadian rhythm parameter(s) (period, amplitude and/or phase) of the series of samples of step (h) and comparing the parameters obtained with circadian rhythm parameters from step (d), and/or with circadian rhythm parameters obtained from a control sample to determine a change 5 in the expression of one or more clock gene(s).

In an embodiment of the present invention, a method is provided of determining pharmacoresponse to an antidepressant in a subject, comprising:

a) obtaining a biological sample from the subject (including but not limited to a skin sample or peripheral blood mononuclear cells);

b) isolating fibroblasts (e.g., skin fibroblasts) from the sample;

c) synchronising the expression of the clock genes in the sample with a first pulse-exposure to a glucocorticoid (including but not limited to dexamethasone, betamethasone, mifepristone, mapracorat, etc.);

d) measuring the expression of a clock gene, which can be, but is not limited to Clock, Bmal, Per and Rev-Erb and any combination thereof, for example, by means of a reporter system (e.g., that allows monitoring of expression driven by a clock gene promoter), or an amplification reaction such as polymerase chain reaction (PCR), from serial samples (e.g., samples are collected at multiple time points after synchronisation, including but not limited to 0, 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc. hours, for example 36 hours, after the synchronisation step); e) analysing the circadian rhythm parameters (period, amplitude and phase) of the series of samples of step (d) and comparing the parameters obtained with circadian rhythm parameters obtained from a control sample (e.g., a subject who does not have or is not suspected of having depression);

f) culturing the sample for a period of time (e.g., until the cells are of sufficient number for further analysis, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, etc. days);

g) resetting (phase-shifting) the expression of the clock gene(s) with a second pulse-exposure of a glucocorticoid (e.g., dexamethasone);

h) measuring the expression of the same clock gene(s) measured in step (d), in serial samples;

i) analysing the circadian rhythm parameters (period, amplitude and phase) of the series of samples of step (h) and comparing the parameters obtained with the circadian rhythm parameters from step (d), and with circadian rhythm parameters obtained from a control sample, wherein decreased amplitude, or lack of a phase-shift in the samples of step (h) as compared with the samples of step (d) or the control sample identifies a subject that may not respond effectively to treatment with an antidepressant drug that is a selective serotonin reuptake inhibitor (SSRI) and may suggest that pharmacotherapy of the subject should be conducted using an alternative antidepressant drug, for example, including, but not limited to a serotonin and norepinephrine reuptake inhibitor (SNRI).

In another embodiment of the present invention, a method is provided of identifying a subject at increased risk of having or developing depression and/or of diagnosing depression in a subject, comprising:

a) obtaining a biological sample from the subject (including but not limited to a skin sample or peripheral blood mononuclear cells);

b) isolating fibroblasts (e.g., skin fibroblasts) from the sample;

c) synchronising the expression of the clock genes in the sample with a first pulse-exposure to a glucocorticoid (e.g., dexamethasone);

d) measuring the expression of a clock gene, which can be but is not limited to Clock, Bmal, Per and Rev-Erb and any combination thereof, for example, by means of a reporter system (that allows monitoring of expression driven by a clock gene promoter), or an amplification reaction (e.g., a polymerase chain reaction (PCR)) in serial samples;

e) analysing the circadian rhythm parameters (period, amplitude and phase) of the series of samples of step (d) and comparing the parameters obtained with circadian rhythm parameters obtained from a control sample;

f) culturing the sample for a period of time;

g) resetting (phase-shifting) the expression of the clock genes with a second pulse-exposure to a glucocorticoid (e.g., dexamethasone);

h) measuring the expression of the same clock gene(s) measured in step (d), in serial samples; and i) analysing the circadian rhythm parameters (period, amplitude and phase) of the series of samples of step (h) and comparing the parameters obtained with the circadian rhythm parameters from step (d), and with circadian rhythm parameters obtained from a control sample, wherein, decreased amplitude of oscillations, or lack of a phase-shift response as compared with the samples of step (d) or the control sample identifies the subject as being at increased risk of having or developing depression and/or as having a diagnosis of depression.

Yet another embodiment of the present invention is a method of guiding the treatment of depression in a subject (e.g., a subject in need thereof), comprising;

a) obtaining a biological sample from the subject (including but not limited to a skin sample or peripheral blood mononuclear cells);

b) isolating fibroblasts (e.g., skin fibroblasts) from the sample;

c) synchronising the expression of clock genes in the sample with a first pulse-exposure to a glucocorticoid (e.g., dexamethasone);

d) measuring the expression of a clock gene, which can be but is not limited to Clock, Bmal, Per and Rev-Erb and any combination thereof, for example, by means of a reporter system, (that allows monitoring of expression driven by a clock gene promoter), or an amplification reaction (e.g., a polymerase chain reaction (PCR)), in serial samples;

e) analysing the circadian rhythm parameters (period, amplitude and phase) of the serial samples of step (d) and comparing the parameters obtained with circadian rhythm parameters obtained from a control sample;

f) culturing the sample for a period of time;

g) resetting (phase-shifting) the expression of the clock genes with a second pulse-exposure to a glucocorticoid (e.g., dexamethasone);

h) measuring the expression of the same clock genes measured in step (d), in serial samples;

i) analysing the circadian rhythm parameters (period, amplitude and phase) of the series of samples of step (h) and comparing the parameters obtained with the circadian rhythm parameters from step (d), and with circadian rhythm parameters obtained from a control sample, wherein decreased amplitude, or lack of a phase-shift in the samples of step (h), identifies a subject that may not respond to treatment with an antidepressant drug that is a SSRI and may indicate that pharmacotherapy of the subject should be conducted using an alternative antidepressant drug, (for example, but not limited to a serotonin and norepinephrine reuptake inhibitor (SNRI);

j) administering a treatment for depression to the subject guided by the results of the first test as described in (i) (e.g., a treatment of the subject with an antidepressant drug that is not a S SRI);

k) obtaining a second biological sample from the subject during and/or following the treatment of step (j);

l) isolating skin fibroblasts from the second sample;

m) synchronising the expression of clock genes in the second sample with a pulse-exposure to a glucocorticoid (e.g., dexamethasone);

n) measuring the expression of a clock gene, which can be but is not limited to Clock, Bmal, Per and Rev-Erb and any combination thereof, for example, with a reporter system (that allows monitoring of expression driven by a clock gene promoter), or an amplification reaction (e.g., a polymerase chain reaction (PCR), in serial samples;

o) analysing the circadian rhythm parameters (period, amplitude and phase) of the series of samples of step (n) and comparing the parameters obtained with circadian rhythm parameters obtained from steps (d) and (h) of the first sample or to a control sample(s);

p) culturing the second sample for a period of time;

q) resetting (phase-shifting) the expression of the clock genes in the second sample with a second pulse-exposure to a glucocorticoid (e.g., dexamethasone);

r) measuring the expression of the same clock genes measured in step (n), in serial samples;

s) analysing the circadian rhythm parameters (period, amplitude and phase) of the series of samples of step (r) and comparing the parameters obtained with circadian rhythm parameters from step (n), and with circadian rhythm parameters obtained from steps (d) and (h) of the first sample or to a control sample; and t) guiding the subject's treatment of depression whereby an improvement/normalisation (for example, an increase in amplitude after the first pulse of dexamethasone, or improved phase-shift response to the second pulse of dexamethasone) in the expression level measured in the second biological sample relative to the expression level measured in the first biological sample leads to maintenance of the treatment and the lack of normalisation/improvement in the expression level measured in the second biological sample relative to the expression level measured in the first biological sample leads to discontinuation of the treatment and/or selection of an alternative drug for treatment.

There are also provided herein kits for performing the methods disclosed herein.

Another object of the invention is to provide a kit for determining a subject's response to treatment with psychotropic drugs, wherein said kit comprises reagents for performing an assay for detecting oscillations in the expression of clock genes, which can be but are not limited to Clock, Bmal, Per and Rev-Erb and any combination thereof. For example, the kit may contain a reporter gene, wherein expression of the reporter gene is driven by clock gene promoters, selected from the group comprising, but not limited to Clock, Bmal, Per and Rev-Erb and any combination thereof. In the reporter gene assay, clock gene expression is firstly synchronised by means of a pulse of glucocorticoids (such as dexamethasone), followed by induction of a phase-shift in clock gene expression by means of a second pulse of glucocorticoids (such as dexamethasone), after which the clock gene oscillation pattern is measured, visualized and compared to a clock gene oscillation pattern of a control sample. Alternatively, a kit may comprise reagents, materials and/or an apparatus/instrument for measuring the expression of clock genes, such as Clock, Bmal, Per and Rev-Erb and any combination thereof by an amplification reaction, such as PCR, or by any other means of measuring protein expression such as ELISA etc. In the PCR based assay, clock gene expression is synchronised either by means of one pulse of glucocorticoids (such as dexamethasone), or by means of one or more pulses, for example two pulses, of glucocorticoids (such as dexamethasone), after which the clock gene oscillation pattern is measured, visualized and compared to a clock gene oscillation pattern of a control sample.

Accordingly, another object of the invention is to provide a kit for determining a subject's response to antidepressant treatment, wherein said kit comprises reagents for performing an assay for detecting oscillations in the expression of clock genes, which can include but are not limited to Clock, Bmal, Per and Rev-Erb and any combination thereof. For example, the kit may include a reporter gene, wherein expression of the reporter gene is driven by clock gene promoters, which can be but are not limited to Clock, Bmal, Per and Rev-Erb and any combination thereof. In the reporter gene assay, clock gene expression is firstly synchronised by means of a pulse of glucocorticoids (such as dexamethasone), followed by induction of a phase-shift in clock gene expression by means of a second pulse of glucocorticoids (such as dexamethasone), after which the clock gene oscillation pattern is measured, visualized and compared to a clock gene oscillation pattern of a control sample. Alternatively, a kit may comprise reagents, materials and/or an apparatus/instrument for measuring the expression of clock genes, such as Clock, Bmal, Per and Rev-Erb and any combination thereof by an amplification reaction, such as PCR, or by any other means of measuring protein expression such as ELISA etc. In the PCR based assay, clock gene expression is synchronised either by means of one pulse of glucocorticoids (such as dexamethasone), or by means of one or more pulses, for example two pulses, of glucocorticoids (such as dexamethasone), after which the clock gene oscillation pattern is measured, visualized and compared to a clock gene oscillation pattern of a control sample.

Another object of the invention is to provide a kit for determining a subject's response to SSRI treatment, wherein said kit comprises reagents for performing an assay for detecting oscillations in the expression of clock genes, which can be but are not limited to Clock, Bmal, Per and Rev-Erb and any combination thereof. For example, the kit may contain a reporter gene, wherein expression of the reporter gene is driven by clock gene promoters, which can be but not limited to Clock, Bmal, Per and Rev-Erb and any combination thereof. In the reporter gene assay, clock gene expression is firstly synchronised by means of a pulse of glucocorticoids (such as dexamethasone), followed by induction of a phase-shift in clock gene expression by means of a second pulse of glucocorticoids (such as dexamethasone), after which the clock gene oscillation pattern is measured, visualized and compared to a clock gene oscillation pattern of a control sample. Alternatively, a kit may comprise reagents, materials and/or an apparatus/instrument for measuring the expression of clock genes, such as Clock, Bmal, Per and Rev-Erb and any combination thereof by an amplification reaction, such as PCR, or by any other means of measuring protein expression such as ELISA, etc. In the PCR based assay, clock gene expression is synchronised either by means of one pulse of glucocorticoids (such as dexamethasone), or by means of one or more pulses, for example two pulses, of glucocorticoids (such as dexamethasone), after which the clock gene oscillation pattern is measured, visualized and compared to a clock gene oscillation pattern of a control sample.

Another object of the invention is to provide a kit for determining a subject's response to fluoxetine treatment, wherein said kit comprises reagents for performing an assay for detecting oscillations in the expression of clock genes, which can be but are not limited to Clock, Bmal, Per and Rev-Erb and any combination thereof. For example, the kit may contain a reporter gene, wherein expression of the reporter gene is driven by clock gene promoters, selected from the group comprising, but not limited to Clock, Bmal, Per and Rev-Erb and any combination thereof. In the reporter gene assay, clock gene expression is firstly synchronised by means of a pulse of glucocorticoids (such as dexamethasone), followed by induction of a phase-shift in clock gene expression by means of a second pulse of glucocorticoids (such as dexamethasone), after which the clock gene oscillation pattern is measured, visualized and compared to a clock gene oscillation pattern of a control sample. Alternatively, a kit may comprise reagents, materials and/or an apparatus/instrument for measuring the expression of clock genes, such as Clock, Bmal, Per and Rev-Erb and any combination thereof by an amplification reaction, such as PCR, or by any other means of measuring protein expression such as ELISA etc. In the PCR based assay, clock gene expression is synchronised either by means of one pulse of glucocorticoids (such as dexamethasone), or by means of one or more pulses, for example two pulses, of glucocorticoids (such as dexamethasone), after which the clock gene oscillation pattern is measured, visualized and compared to a clock gene oscillation pattern of a control sample.

Still another object of the invention is a method for screening an antidepressant for the ability to normalise alterations in circadian rhythm by measuring oscillations in the expression of clock genes, which can be but are not limited to Clock, Bmal, Per and Rev-Erb and any combination thereof, in a sample from a subject before, after and/or during treatment of the sample and/or the subject with said antidepressant. For example, an altered phase-shift response (period, amplitude and/or phase), including the lack of a phase-shift response compared to a control sample, as determined by the expression of clock genes, selected from the group comprising, but not limited to Clock, Bmal, Per and Rev-Erb and any combination thereof, following synchronisation and resetting of clock gene expression by means of one or more pulses of glucocorticoids (such as dexamethasone) may be used to screen for antidepressant drugs that normalise the former alterations in circadian rhythm.

There is also provided herein a method of assessing a subject's alteration in circadian rhythm comprising actigraphy. Said method may be used as a complement to a method for identifying alterations in circadian rhythms that are reflected in changes in the expression of clock genes, for further improving the determination of alterations in circadian rhythm, finding several uses e.g., in determining pharmacoresponse to a drug as disclosed herein. Accordingly, said method may comprise measuring the changes in expression of one or more clock gene(s) as disclosed herein and estimating the intrinsic rhythmicity of spontaneous activity by using an actigraphy device on said subject.

BRIEF DESCRIPTION OF THE DRAWINGS

FIGS. 1A and 1F. Dexamethasone (DEX)-exposed mice show depression-like behavior and impaired neurogenesis that are not reversed by antidepressant treatment. FIG. 1A DEX-exposed mice show depression-like behavior at 12 months (mo), but not earlier. Chronic treatment with fluoxetine (FLX) decreases the immobility time in controls, but not in DEX-exposed mice. FIG. 1B Tail suspension test in mice aged 12 mo. FIGS. 1C-1D Impaired hippocampal neurogenesis in DEX-exposed mice aged 12 mo. Developmental exposure to DEX reduces both progenitor cell proliferation (EdU+ cell number, C) and neuronal differentiation (DCX-positive cell number, D). Note that DEX-exposure also reduces the complexity of the dendritic arborisation of newly generated neurons (inset). Chronic antidepressant treatment with FLX reduces neurogenesis in controls, but has no effect in DEX-exposed mice. FIG. 1E GR expression in the hippocampus is lower in DEX-exposed mice than in controls. FIG. 1F DEX-exposed mice have lower levels of corticosterone metabolites in the feces and display no circadian fluctuations in GC secretion. FIGS. 1A, 1C, 1D—factorial ANOVA followed by contrast analysis. FIGS. 1B, 1E—student's t-test; FIG. 1F—mixed model ANOVA (repeated measures between-group design), followed by unequal N HSD post-hoc test.

FIG. 2A: The amplitude and acrophase of circadian fluctuations measured by cosinor analysis at baseline and after resetting the internal clock. As expected, the amplitude increases in controls upon resetting the internal clock. In contrast, DEX-exposed mice have similar amplitude at baseline and after resuming the LD cycle. FIGS. 2B: Acrophase occurrence at baseline and immediately after resuming the LD cycle. The acrophase occurs later, and is not different between baseline and after resetting the internal clock in DEX-exposed mice after 3 mo. Where "baseline" is before the DD period; "reset" is immediately after resuming the LD cycle after the DD period. FIG. 2C: Expression of clock genes in the hippocampus. The cyclic expression of Clock, Bmal1, Per1/2, and Rev-Erb α is abolished in DEX-exposed mice. FIGS. 2A, 2B—mixed model ANOVA (repeated measures between-group design), followed by unequal N HSD post-hoc test; N=7-8/time point. FIG. 2C—factorial ANOVA followed by contrast analysis; N=4/group.

FIG. 3A: Representative double-plotted heat maps in 3 mo mice, one control and one DEX-exposed mouse (indicated on top of each graph). Each point represents the cumulative number of visits recorded in 15 min time bins. LD—12:12 h light:dark cycle; DD—constant darkness; LD*—forced resynchronisation, induced by resuming the LD cycle after extended DD period. FIG.3B: Internal period of spontaneous activity in the home cage. The period is shorter in DD compared with LD cycle in young controls (3 and 5 mo), but not in DEX-treated mice. At 12 mo, the period is shorter than 24 h at baseline in both controls and DEX-exposed mice, but returns to 24 h upon resuming the LD cycle after 14 days in DD only in controls. FIG. 3C: Scale invariance in the spontaneous locomotor activity in the home cage. A high scaling exponent (approaching 1) is suggestive for strong underlying regularity and long-term positive correlations, while a low scaling exponent indicates less regularity and weak long-term correlation (approaching 0.5 for random fluctuations). The scaling exponent does not vary between LD and DD in control mice, which indicates that the internal clock maintains a robust pacemaker function regardless of the drive by environmental stimuli. In contrast, the scaling exponent decreases during DD in DEX-exposed mice. This effect is consistently detected at all ages tested. The fact that the scaling exponent is lower during DD than in LD suggests that the regularity in spontaneous activity of DEX-exposed mice is driven by external, presumably environmental cues in LD conditions.

FIG. 4A: Bioluminescence signal in fibroblasts derived from mPer2::Luc knock-in mice. Illustrative recording spanning 10 days after the synchronisation with a single pulse of DEX (arrow). Note the self-sustained oscillations in bioluminescence driven by mouse Per2 promoter. The signal intensity is normalised to the maximum intensity recorded in the culture dish. FIG. 4B: Predictable deviations from normal pattern of oscillations after a single DEX pulse (arrow). Lower amplitude indicates lower expression of clock genes or poor synchronisation (C, D). Predicted oscillations as can be observed after double DEX pulse (arrows). The second pulse should induce a complete phase reset, without affecting the parameters of circadian oscillations. However, the second pulse of DEX is followed by either changes in the phase FIG. 4C, or amplitude FIG. 4D of oscillations, indicating alterations in the response to entraining stimuli.

DETAILED DESCRIPTION OF THE INVENTION

I. Definitions

Figure 2A:
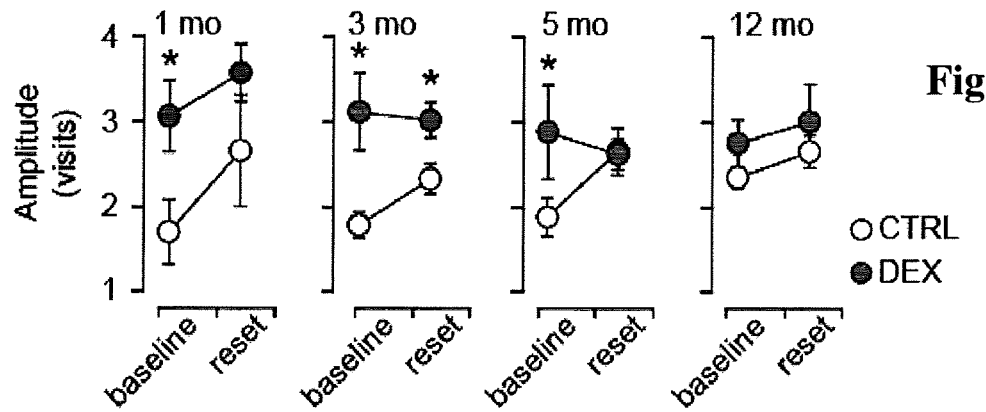
FIGS. 2A-2C. Rigid synchronisation with the LD cycle and lack of circadian fluctuations in clock gene expression in DEX-exposed mice.

Unless otherwise defined, all technical and scientific terms used herein have the same meaning as commonly understood by one of ordinary skill in the art to which this invention pertains. As used herein, "a" or "an" or "the" can mean one or more than one. For example, "a" cell can mean one cell or a plurality of cells.

Also as used herein, "and/or" refers to and encompasses any and/or all possible combinations of one or more of the associated listed items, as well as the lack of and and/or combinations when interpreted in the alternative ("or"). Furthermore, the term "about" as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

The term "neuropsychiatric disorder" refers to mental, emotional, and/or behavioral abnormalities. These include but are not limited to bipolar disorder, schizophrenia, schizoaffective disorder, psychosis, depression, stimulant abuse, alcoholism, panic disorder, generalized anxiety disorder, attention deficit disorder, post-traumatic stress disorder, and Parkinson's disease.

The term "depression" as diagnosed in practicing the methods and compositions of the invention includes all diseases and conditions that are associated with depression. These diseases or disorders comprise major depression, major depressive disorder, dysthymic disorder, depressive episodes of bipolar disorders and depressive episodes associated with other mood disorders, including seasonal mood disorders and mood disorders due to a general medical condition and substance induced mood disorder.

The terms "selective serotonin reuptake inhibitor" or "SSRI" refer to a class of drugs with a mechanism of action of inhibiting reuptake of serotonin released in neuronal synapses and is used in pharmacotherapy of, for example, major depressive disorder. Non-limiting examples of SSRI class drugs are fluoxetine (Prozac™), citalopram (Celexa™, Cipramil™), escitalopram (Cipralex™), paroxetine (Paxil™), sertraline (Zoloft™) etc.

The term "psychotropic drug" refers to any drug capable of affecting the mind, emotions, and/or behavior. The main classes of psychotropic drugs include but are not limited to, antidepressants (with several subclasses), antianxiety drugs, antimanic/mood stabilizers, antipsychotics, and stimulants.

The term "treatment" as used herein refers to partially or completely ameliorating at least one symptom of, partially or completely treating or curing and/or preventing the development of a disease or a condition, for example, depression.

The term "subject" and the term "patient" and the term "individual" may include any mammal, including humans and are used interchangeably. Herein, a subject from which a biological sample originates may be suffering from a neuropsychiatric disorder, e.g. depression, or may be in a pre-clinical stage thereof and/or is to be treated or has been treated with a psychotropic drug, such as an antidepressant.

A "control sample" may originate e.g. from a subject who does not have or is not suspected of having a neuropsychiatric disorder, such as depression.

The term "circadian rhythm" refers to the diurnal rhythm of events and biochemical phenomena displayed by living organisms. In particular, it refers to the synchronisation of spontaneous activity and physiological processes, including, but not limited to secretion of hormones, such as, but not limited to glucocorticoids (stress hormones synthetized and secreted by the cortex of the adrenal gland), with the light-dark cycle, which is mediated by the suprachiasmatic nucleus (SCN). Circadian rhythms or central clock functions are driven by the molecular clock machinery and employs the expression of clock genes.

The term "circadian entrainment" refers to the synchronisation of circadian rhythms with an external pacemaker. An external pacemaker is any event/process that can drive the synchronisation of internal rhythms (e.g., light-dark cycle or regular feeding). The entrained circadian rhythms (i) should be self-sustained oscillations (i.e., preserve the period, phase and amplitude for a length of time after removing the external pacemaker); (ii) have the same period as the external pacemaker; and (iii) have a consistent phase relationship with the external pacemaker. Therefore, immediate resetting of the phase may be indicative of impaired entrainment (i.e., the oscillations are not self-sustained and parameters change immediately in response to a change in the external pacemaker's activity).

The term "clock genes" in mammals includes Per genes (Per1, Per2, Per3), Clock gene, Bmal genes (Bmal1, Bmal2, Bmal3), Cry genes (Cry1, Cry2), Rev-Erb genes (Rev-erbα, Rev-erbβ), and the like. Among these, BMAL1 (a transcript of the Bmal1 gene; the same shall apply hereinafter) has been suggested to form a dimer with CLOCK (a transcript of the Clock gene; the same shall apply hereinafter) and to activate the expression of Per gene, Cry gene or the like via E-box (the promoter region of Per1 gene).

The term "BMAL-1" refers to a PAS domain/bHLH protein that heterodimerizes with CLOCK to form a transcription complex that positively regulates the circadian clock in the SCN and dimerizes with NPAS2 and other proteins in other areas of the brain and peripheral tissues.

The term "PER" refers to the Periodic protein(s) that are regulated by the BMAL1/CLOCK complex. The PER protein acts with CRY to form a negative transcriptional regulatory complex that oscillates in expression with CLOCK and NPAS2. The PER proteins are expressed in both central and peripheral clock tissues.

The term "AhR" refers to aryl hydrocarbon receptor (AhR) and is a ligand dependent transcription factor belonging to the bHLH-family that mediates a wide range of critical cellular events in response to halogenated aromatic hydrocarbons and nonhalogenated polycyclic aromatic hydrocarbons. Upon binding to its ligand, AhR translocates from the cytoplasm to the nucleus. Inside the nucleus, liganded AhR forms a heterodimer with Ah receptor nuclear translocator (Arnt). The former heterodimer then binds to a regulatory element, Ah response element (AhRE), within target genes either to enhance or to attenuate transcription of these genes. Responses mediated by AhR include expression of P450 family genes.

The term "reporter gene" means a gene that is normally not expressed by the cell system under investigation, and whose expression is driven by a pre-determined promoter region and can therefore be assayed to assess the function of specific transcription factors.

II. Compositions

In light of the difficulties that are generally encountered when deciding on a suitable therapy for the treatment of diseases having a neurodevelopmental origin, including depression, it was decided to investigate if there could be a way of easing such a procedure.

Therefore, in this invention, two animal models of developmental neurotoxicity were established, either through exposure to methylmercury (MeHg; a known neurotoxic environmental contaminant), or to dexamethasone ((DEX); a synthetic glucocorticoid receptor agonist). While both models lead to depression-like behavior, the differences between the models can be summarized as follows:

1) in the MeHg model, the depression-like behavior is detectable in young adults (2-3 months), and is reversed by antidepressant treatment with fluoxetine (FLX) whereas;
2) in the DEX model, the depression-like behavior is detectable only in middle-aged mice (12 months), and is not reversed by FLX. The depression-like behavior in DEX-exposed mice is associated with alterations in circadian entrainment, which are not observed in MeHg-exposed depressed mice. Importantly, the circadian rhythm alterations in DEX-exposed mice were observed already from the age of 1.5 months and increased in severity until 12 months (middle-age), when depression-like behavior was documented. In middle-aged mice the inventors found that the intrinsic rhythmicity of spontaneous activity was significantly increased in the presence of a light-dark cycle, indicating a more rigid dependence on environmental light intensity. In addition, under constant light-dark cycle conditions (i.e., steady entrainment), the period of spontaneous activity was significantly shorter than 24 h, indicating that the central clock was not reset as in control mice. Importantly, the cyclic fluctuations in clock gene expression were not synchronised with the light-dark cycle already at the age of 3 months, or prior to development of depression-like behavior.

Next this invention assessed the function of the molecular clock in ex vivo fibroblast preparations from control and DEX-exposed mice. All skin fibroblasts express functional molecular clock machinery, while the parameters differ slightly among cells. Therefore, oscillations in clock gene expression can be documented in individual cells, while oscillations can only be detected at population level (by qPCR or using reporter systems) after synchronisation using DEX, serum shock, or change of medium. Concurrent with the alterations in circadian entrainment of spontaneous activity in the DEX-exposed mouse model, the amplitude of oscillations in clock gene expression was also attenuated in DEX-exposed mice, as compared to controls (see FIG. 5).

In addition, the experimental findings of this invention further comprised performing the ex vivo fibroblast assay in mice using a reporter assay system (see FIG. 4A), as well as in fibroblast preparations from a human subject (see FIG. 7), corroborating the promise and robustness of the method of this invention in measuring expression of clock genes, or alterations thereof, in both animal and human models.

Based on the experimental findings of this invention, including that (i) the depression-like behavior in the DEX-exposed animal model of depression was resistant to pharmacological treatment with one of the most commonly prescribed antidepressants, fluoxetine, and (ii) alterations in circadian rhythm and the expression of clock genes could be detected in in vitro (ex vivo) assays using fibroblasts from the DEX-exposed animal model, embodiments of this invention are provided that include identifying alterations in circadian rhythms that are reflected in changes in the expression of clock genes in order to 1) diagnose depression in a subject (e.g., at an early stage, even prior to development of clinical symptoms; 2) determine and/or modulate a subject's pharmacoresponse to a psychotropic drug, such as an antidepressant; and 3) develop and/or implement protocols for the treatment of a neuropsychiatric disorder, such as depression.

In some embodiments, the present invention provides a method of screening antidepressants, for instance, including but not limited to, antidepressants undergoing pre-clinical development, clinical testing or for antidepressants currently in clinical use. In yet another embodiment, the present invention provides a method of screening psychotropic drugs, for example, but not limited to, psychotropic drugs undergoing pre-clinical development, clinical testing or for psychotropic drugs currently in use in patients.

An example of a psychotropic drug is a selective serotonin reuptake inhibitor (SSRI), such as Fluoxetine.

In one embodiment of the present invention, a method is provided comprising:

a) obtaining a biological sample from a subject, such as a skin sample;
b) isolating skin fibroblasts from the sample;
c) synchronising the expression of the clock genes in the sample by means of pulse-exposure to a glucocorticoid, including dexamethasone;
d) measuring the expression of clock genes, which can be but are not limited to Clock, Bmal, Per and Rev-Erb and any combination thereof, using, for example, an amplification reaction, such as polymerase chain reaction (PCR), from serial samples;
e) analysing the circadian rhythm parameters (period, amplitude and phase) in the series of samples of step (d) and comparing the parameters obtained with circadian rhythm parameters obtained from a control sample.

In another embodiment of the present invention, a method is provided comprising:

a) obtaining a biological sample from a subject, such as a skin sample;
b) isolating skin fibroblasts from the sample;
c) synchronising the expression of the clock genes in the sample by means of pulse-exposure to a glucocorticoid, including dexamethasone;
d) measuring the expression of clock genes, which can be but are not limited to Clock, Bmal, Per and Rev-Erb and any combination thereof, for example, using a reporter system (that allows monitoring of expression driven by a clock gene promoter), or an amplification reaction, such as polymerase chain reaction (PCR), from serial samples;
e) analysing the circadian rhythm parameters (period, amplitude and phase) in the series of samples of step (d) and comparing the parameters obtained with circadian rhythm parameters obtained from a control sample;
f) culturing the sample for a period of time;
g) resetting (phase-shifting) the expression of the clock genes with a second pulse-exposure of a glucocorticoid (e.g., dexamethasone);
h) measuring the expression of the same clock genes measured in step (d), in serial samples; and
i) analysing the circadian rhythm parameters (period, amplitude and phase) of the series of samples of step (h) and comparing the parameters obtained with circadian rhythm parameters from step (d), and with circadian rhythm parameters obtained from a control sample.

More specifically, there is provided herein a method for identifying alterations in circadian rhythms in a subject that are reflected in changes in the expression of one or more clock gene(s) in said subject, said method comprising: a) obtaining a biological sample from the subject; b) isolating fibroblasts from the sample to provide a second sample; c) synchronizing the expression of the clock genes in the second sample by means of a first pulse-exposure of said second sample to a glucocorticoid; d) measuring the expression of clock genes from serial samples from said second sample collected at multiple time points after synchronization and; e) analysing a circadian rhythm parameter(s) (period, amplitude and/or phase) in the series of samples of step (d) and comparing the parameters obtained with circadian rhythm parameters obtained from a control sample to determine a change in the expression of one or more clock gene(s).

There is also provided a method for identifying alterations in circadian rhythms in a subject that are reflected in changes in the expression of one or more clock gene(s) in said subject comprising the following steps: a) obtaining a biological sample from the subject; b) isolating fibroblasts from the sample to provide a second sample; c) synchronising the expression of the clock genes in the second sample by means of a first pulse-exposure of said second sample to a glucocorticoid; d) measuring the expression of clock genes from serial samples from said second sample collected at multiple time points after synchronisation and; e) analysing a circadian rhythm parameter(s) (period, amplitude and/or phase) in the series of samples of step (d) and comparing the parameters obtained with circadian rhythm parameters obtained from a control sample to determine a change in the expression of one or more clock gene (s), f)

culturing the second sample for a period of time; g) resetting (phase-shifting) the expression of the clock genes with a second pulse-exposure of said second sample to a glucocorticoid; h) measuring the expression of the same clock genes measured in step (d), in serial samples from said second sample collected at multiple time points; and i) analysing a circadian rhythm parameter(s) (period, amplitude and/or phase) of the series of samples of step (h) and comparing the parameters obtained with circadian rhythm parameters from step (d), and/or with circadian rhythm parameters obtained from a control sample to determine a change in the expression of one or more clock gene (s).

Said method may be used to determine a subject's pharmacoresponse to a psychotropic drug, such as an antidepressant, and may hence comprise steps a) to i) of a method disclosed herein. Such an antidepressant may be a serotonin uptake receptor inhibitor (SSRI), such as fluoxetine. Therein, in step i) of said method, a decreased amplitude, and/or lack of a phase-shift in the series of samples of step (h) as compared with the samples of step (d) and/or the control sample may identify a subject that may not respond effectively to treatment with an antidepressant drug e.g. a selective serotonin reuptake inhibitor (S SRI) and may suggest that pharmacotherapy of the subject should be conducted using an alternative antidepressant drug, such as a serotonin and norepinephrine reuptake inhibitor (SNRI).

Said method may also be used for identifying a subject at increased risk of, such as prior to, having or developing depression and/or diagnosing depression in a subject, and may hence comprise steps a) to i) of a method disclosed herein. Therein, in step i) of said method, a decreased amplitude of oscillations, and/or lack of a phase-shift response in the samples of step h) as compared with the samples of step (d) and/or the control sample may identify the subject as being at increased risk of having or developing depression and/or as having a diagnosis of depression.

There is also provided herein a method wherein a subject's alteration in circadian rhythm is used for guiding the treatment of depression in a subject as further disclosed herein, said method comprising steps a) to i) of a method as disclosed herein, wherein in step i) of said method a decreased amplitude, and/or lack of a phase-shift in the samples of step (h) as compared with the samples of step (d) and/or the control sample, identifies a subject that may not respond to treatment with an antidepressant drug, e.g an S SRI, and may indicate that pharmacotherapy of the subject should be conducted using an alternative antidepressant drug, said method further comprising the steps of j) administering a treatment for depression to the subject guided by the results of step (i); k) obtaining a further biological sample from the subject during and/or following the treatment of step (j); l) isolating fibroblasts from the further biological sample, to provide a third sample; m) synchronising the expression of clock genes in the third sample with a pulse-exposure of said third sample to a glucocorticoid; n) measuring the expression of a clock gene, in serial samples of said third sample collected at multiple time points; o) analysing the circadian rhythm parameters (period, amplitude and/or phase) of the series of samples of step (n) and comparing the parameters obtained with circadian rhythm parameters obtained from steps (d) and (h) of the second sample and/or to a control sample(s); p) culturing the third sample for a period of time; q) resetting (phaseshifting) the expression of the clock genes in the third sample with a second pulse-exposure of said third sample to a glucocorticoid; r) measuring the expression of the same clock genes measured in step (n), in serial samples collected at multiple time points; s) analysing the circadian rhythm parameters (period, amplitude and/or phase) of the series of samples of step (r) and comparing the parameters obtained with circadian rhythm parameters from step (n), and/or with circadian rhythm parameters obtained from steps (d) and (h) of the second sample and/or to a control sample; and t) guiding the subject's treatment of depression whereby an improvement/normaliszation in the expression level measured in the second further biological sample relative to the expression level measured in the first second biological sample leads to maintenance of the treatment and the lack of normalisation/improvement in the expression level measured in the second further biological sample relative to the expression level measured in the first second biological sample leads to discontinuation of the treatment and/or selection of an alternative drug for treatment.

It is also to be understood that fibroblasts isolated from the biological sample are used in the context of the method. Said fibroblasts may be extracted from a previous biopsy, and are substantially pure even though sometimes it may contain some minor remains from the biopsy.

There are provided methods that are performed in vitro, as further mentioned herein.

Serial samples are then obtained from a culture containing said isolated fibroblasts, at multiple time points after synchronisation and/or re-setting using glucocorticoids as further mentioned 10 herein. Serial samples may be taken e.g., including but not limited to at 0, 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, hours, for example 36 hours, after the synchronisation steps and/or after the resetting. Culturing of a sample comprising fibroblasts prior to and/or between synchronisation and resetting may be performed e.g., for 1, 2, 3, 4, 5, 6, 7, 8, 9, 10, 11, 12, 13, 15 14, 15, 16, 17, 18, 19, 20, 21, 22, 23, 24, 25, 26, 27, 28, 29, 30, or 31 days. Further examples are provided in the experimental section.

The changes in the expression of one or more clock gene(s) may be detected as oscillations in the expression of one or more clock gene(s). This may be presented as an oscillation pattern that may e.g., be used in comparison with an oscillation pattern derived from a healthy subject, such as a subject that is not likely to suffer from a neuropsychiatric disorder, e.g., depression. This is exemplified in the experimental section. Examples of a biological sample are e.g., a skin sample or a biological sample that comprises peripheral blood mononuclear cells. Said glucocorticoid may e.g., be dexamethasone, betamethasone, mifepristone and mapracorat. Examples of how to detect changes of expression of one or more clock gene(s) are mentioned herein, e.g. in the experimental section. Hence, the expression of one or more clock gene(s) may be measured by means of e.g., a reporter system or by a Polymerase Chain Reaction (PCR). The measuring of the expression of a clock gene may be performed by means of a reporter system, such as a reporter system that allows monitoring of expression driven by a clock gene promoter. Said clock gene may comprises CLOCK, BMAL, PER and REV_ERB (Clock, Emal, Per and Rev-Erb) and/or any combination thereof.

In the former embodiments of the invention, the first pulse of DEX synchronises the expression of clock genes across the entire population of cultured cells and ensures that the oscillations in clock gene expression become self-sustained. The period and amplitude of the self-sustained oscillations further provide information about the molecular clock function per se, for instance whether it is possible to synchronise the expression of clock genes across the fibroblast population at all. The information generated by the first synchronisation can be unspecific as, for instance, lower amplitude in the oscillations of clock gene expression can be due to either lower expression of clock genes (e.g., due to mutations in either the body, or promoter region, of one or more of the clock genes), or due to a diminished response to entraining stimuli (e.g., due to lower expression of the glucocorticoid receptor, or downstream negative modulation of glucocorticoid receptor activity). Therefore, the response to resynchronisation with a second pulse of DEX (i.e. a gluccocorticoi) can be critical, as it yields additional information pertaining to the robustness of the molecular clock in relation to resetting. While the molecular clock has a degree of adaptability, it should also be stable and resist changes to a certain extent and wherein, either too little resistance (facilitated re-entrainment), or excessive rigidity (resistance to re-entrainment) can indicate pathological changes. Thus, lack of phase reset after the second pulse of DEX (i.e. a gluccocorticoi) can indicate that the skin fibroblasts are unresponsive to entraining stimuli, meanwhile a normal phase reset response, but with low amplitude, can indicate a mutation in clock genes that render the re-entraining stimuli ineffective.

The inventors anticipate that refinement of the methods as described herein would identify critical time points for determining the expression, or alterations thereof, of clock genes, comprising, but not limited to Clock, Bmal, Per and Rev-Erb. The series of samples as referred to in the embodiments of the invention can further comprise one or more samples taken at one or more time points for determining the expression, or alterations thereof, of clock genes, comprising, but not limited to Clock, Bmal, Per and Rev-Erb. As such, the circadian rhythm parameters measured could be one or more of period, amplitude and/or phase.

Yet another embodiment of the invention provides a method of determining expression of clock genes, which can be but are not limited to Clock, Bmal, Per and Rev-Erb, or alterations thereof, to identify a subject at risk of developing neuropsychiatric disorders (e.g., diagnosing a subject) and/or to determine a subject's pharmacoresponse as well as monitoring treatment of a subject, in response to a psychotropic drug. Further embodiments include analysing the clock gene expression profile in a population of subjects that have a neuropsychiatric disorder and identifying a correlation between a clock gene expression profile and the neuropsychiatric disorder and then looking for the clock gene expression profile in a subject, wherein the presence of the clock gene expression profile in the subject identifies the subject as having the neuropsychiatric disorder or as being at increased risk (relative to a subject that lacks the clock gene expression profile) of developing the neuropsychiatric disorder.

Still another embodiment of the invention provides a method of determining expression of genes that regulate circadian rhythms, without being directly involved in the clock gene feedback loops, or alterations thereof, to identify subjects at risk of developing neuropsychiatric disorders, including depression and/or to determine the patient's pharmacoresponse to a psychotropic drug, including antidepressants. One such pathway that regulates circadian rhythms, without being directly involved in the clock gene feedback loops, is the aryl hydrocarbon receptor (AhR) pathway, including AhR, AhR repressor (AhRR), AhR nuclear translocator (ARNT) and downstream-regulated genes, such as cytochrome p450 (CYP) enzymes. The AhR pathway is connected with the molecular clock machinery in the brain and it appears to regulate neuronal plasticity (including hippocampal neurogenesis and learning). The pathway is also particularly relevant in other cell types, such as fibroblasts, including skin fibroblasts.

There is also provided a method wherein a subject's alterations in circadian rhythms is used to stratify patients with a specific neuropsychiatric disorder in order to enrich patients for better response in a clinical trial.

Another object of this invention was to use an alternative method of assessing a subject's alterations in circadian rhythm comprising actigraphy. Wrist actigraphy assesses the modulation of activity under the influence of multiple intrinsic and extrinsic factors (ranging from light-dark cycle to social interactions and meal times). This invention demonstrates that (wrist) actigraphy can be a valuable tool in determining alterations in circadian rhythm in a subject diagnosed with a neuropsychiatric disorder, such as seasonal depression, compared to a healthy control (see FIGS. 6A-6D).

Following on from the use of actigraphy as an alternative method of assessing a subject's alterations in circadian rhythm, another objective of this invention is to combine the use of actigraphy with measuring the expression of clock genes in primary fibroblast cultures (e.g., also measuring the internal clock at a molecular level) as described in this invention. Said actigraphy device may be used to estimate the intrinsic rhythmicity of spontaneous activity of a subject, such as wherein said actigraphy device is worn for about 5-7 days. The former combination of actigraphy and a method of measuring expression of clock gene expression in primary fibroblast cultures can be expected to increase the precision (positive- and negative-predictive value) and the accuracy in order to 1) diagnose depression in a subject (e.g., at an early stage, even prior to development of clinical symptoms; 2) determine and/or modulate a subject's pharmacoresponse to an antidepressant; and 3) develop and/or implement protocols for the treatment of depression.

The raw activity data from the actigraphy may be exported and/or analysed using one or more of the following algorithms: cosinor analysis; unbiased periodogram analysis; and detrended fluctuation analysis, or any combination thereof. The results from the actigraphy analysis may be used to derive a behavioral profile in order to estimate the risk of a subject developing a neuropsychiatric disorder. The results from the actigraphy analysis may also be used to derive a behavioral profile in order to guide the treatment of a neuropsychiatric disorder.

III. Kits and Assays

The invention provides kits for determining a subject's responsiveness to a neuropsychiatric disorder therapy, for instance antidepressants (i.e. against depression). Hence, there is provided herein a kit for performing a method as disclosed herein, said kit comprising reagents for performing an assay for detecting oscillations in the expression of one or more clock gene (s), and optionally instructions for use. As an example, kits of the invention can be used to identify individuals at risk of developing depression and/or to evaluate or determine the optimal treatment, e.g., drug regimen, drug scheduling or treatment protocol, when a subject is diagnosed with a neuropsychiatric disorder, such as depression.

The kit can comprise material; optimised tools and reagents for, for instance, cell culture (plastic ware, reagents for infection, vector construct); primers for rtPCR, or reagents suitable for use in, for instance, an ELISA assay, to determine clock gene expression and a glucocorticoid, for example, dexamethasone, as well as analytical tools (software) for computing and analysing the parameters derived from the measurements, for instance bioluminescence. The kit can comprise suitable packaging material. The kit can comprise instructional material for use of said kit, e.g., instructions on practicing the methods of the invention.

A reporter gene assay employing transient transfection into various cells from yeast to mammals, including primary human cells, is a standard procedure. The regulatory regions, i.e., gene promoter and enhancer are cloned upstream of the structural part of a gene encoding a reporter protein (cf. e.g., Muhlhardt, Der Experimentator: Molekularbiologie, Gustav Fischer Verlag 1999), for example, II-galactosidase, firefly luciferase, *renilla* luciferase, a fluorescent protein (e.g. GFP, EGFP, EYFP, etc.), human growth hormone, CAT (chloramphenicolacetyltransferase), TAT (tyrosylaminotransferase), alkaline phosphatase including SEAP, and peroxidase. Suitable eukaryotic cell lines include immortalized tumor cell lines, listed for example in the catalogues of ATCC and ETCC, including but not limited to the cell lines HeLa, HEK, L929, NIH3T3, COSI, COS7, HepG2, H4-II-E-C3, Saos, K562, SK-N-MC, HT22 or CV-I. As an alternative to transient transfection assays, an in vitro transcription/translation system may be adapted, or stably transfected cell lines may be used accordingly. A number of methods are established to generate cell lines stably transfected with a reporter gene plasmid.

A kit provided herein may also comprise an actigraphy device.

EXAMPLES

Some methods and materials are described below, although methods and materials similar or equivalent to those described herein can be used in the practice or testing of the present invention. The following examples are offered to illustrate, but not limit the claimed invention.

Example 1

DEX-Exposed Mouse Model of Depression
Materials and Methods
Animals and Treatments All experiments were performed in agreement with European and Swedish national regulation following approval by the local Animal Ethics Committee.

Timed-pregnant female C57Bl/6 mice (N=34/treatment) (Charles River, Germany) were injected subcutaneously with 0.05 mg/kg/day dexamethasone (DEX; Sigma-Aldrich, Sweden) from gestational day (GD) 14 until delivery. The delivery day was recorded as postnatal day (PND) 0. The litters were culled to 4 pups/litter at PND3. The pups were weighed at PND3, 7, 14, and 21. At weaning (PND21), the mice were implanted subcutaneously with sterile radio-frequency identification (RFID) tags (Trovan Unique 100A, Trovan Ltd., UK) under brief isoflurane anesthesia. The transponders allowed unambiguous identification of animals and were also used for monitoring the activity in homecage environment. After implantation, the pups were redistributed to new cages so that each cage would house a maximum of 5 mice originating from different litters, and the distribution was maintained throughout the study. The mice were kept in an animal facility under 12 h:12 h light-dark (LD) cycle (light intensity 50 lx; light on at 6 a.m.) at constant temperature ($22\pm1°$ C.) and humidity ($50\%\pm5\%$). The circadian zeitgeber ("time-giver") time (ZT) 0 corresponds to the subjective sunrise, i.e., the onset of the light phase.

Behavioral Testing

The mice were first screened in a battery of behavior tests, as described below.

Depression-Like Behavior.

Adult male mice aged 7 weeks, 3 mo, or 12 mo were tested for depression-like behavior in the forced swim tests (FST). Briefly, the animals were individually placed in glass cylinders (24 cm height, 12 cm diameter) filled with water ($23.5°$ C.) to a depth of 16 cm. The animals were exposed to a 15 min pretest followed by a 6 min test 24 h later. Test sessions were videotaped and analysed offline by one investigator who was blind to the treatment and exposure conditions. Immobility was defined as passive floating for at least 2 s. After documenting depression-like behavior at the age of 12 mo, the animals were treated with fluoxetine (FLX; a selective serotonin re-uptake inhibitor antidepressant) dissolved in drinking water (80 mg/L) for 21 days before repeating the test. In addition to FST, depression-like behavior was tested in a tail-suspension test (TST), as described below.

For TST, the mice were allowed to acclimatize in the testing room for at least 30 min before the experiment. The mice were suspended by the tail 15 cm above the table (using adhesive tape placed approx. 2 cm from the base of the tail). Soft padding was provided in order to prevent injuries in case the animal escaped or fell down because of tape failure. After 6 min, the animal were released and placed in the homecage. The experiment was videotaped and the analysis was performed offline by a rater blind to the experimental conditions. The immobility time was estimated by summing the duration of immobility bouts longer than 3 s. Animals that displayed persistent climbing on the tail (total duration exceeding 72 s), or escaped were excluded from analysis.

Analysis of Hippocampal Neurogenesis and Glucocorticoid Receptor (GR) Expression The subgranular zone (SGZ) of the hippocampal dentate gyrus (DG) is one of the brain regions that retain the neurogenic potential in adult animals. To investigate neurogenesis, progenitor proliferation and the maturation of newly generated neurons in the DG were estimated by immunohistochemical methods as described below.

Immunohistochemistry for Quantifying Hippocampal Neurogenesis and GR Expression

The subgranular zone (SGZ) of the hippocampal dentate gyrus (DG) is one of the brain regions that retain the neurogenic potential in adult animals. Hippocampal neurogenesis was assessed by quantifying the proliferation of progenitor cells (labeled by EdU uptake when undergoing cell division). The development of newly generated neurons was investigated by counting the DCX-positive neuroblasts throughout the SGZ and the granule cell layer of the DG.

Control and DEX-exposed 12 mo mice were killed by an overdose of anesthetic (sodium pentobarbital, 150 mg/kg). The brain was fixed by intracardial perfusion with ice-cold paraformaldehyde (4% in PBS, 100 ml/animal), then post-fixed overnight at 4° C. in paraformaldehyde before cryoprotection in 10% buffered sucrose (overnight at 4° C.) and stored at −80° C. until processing. The brains were cut in sagittal sections (20 μm thick) with a cryostat (Leica CM3050). Equally spaced series (200 μm between consecutive slices) were collected starting from the first occurrence of the hippocampal structure until the dorsal hippocampal commissure (lateral 3.5-0 mm in stereotaxic coordinates) and stored at −80° C. until processing. The slides were air-dried for 30 min at room temperature, then rehydrated for 10 min in PBS. Before the application of the primary antibody, the unspecific labeling was blocked by incubation for 2 h with normal serum of the species in which the secondary antibody was raised (in 0.3% Triton-X in PBS, 50 μl/slice). The slices were then incubated with the primary antibodies at 4° C. (see Table 1 for incubation time and dilution for each antibody). After washing, the tissue slices were incubated with the secondary antibody for 2 h at room temperature. The excess secondary antibody was removed by repeated washing with PBS, then counterstained using a fluorescence nuclear dye (DAPI, Sigma-Aldrich, Germany) before mounting the slides with fluorescence mounting medium (Dako, Golstrup, Denmark). The specificity of the staining was verified by using the same protocol, except omitting the primary antibody from the cocktail for the first incubation.

Progenitor proliferation was assessed by counting EdU-positive cells in the SGZ (defined as a 2 cell-diameter layer subjacent to the granule cell layer of the DG) after pulse-labeling by systemic administration of EdU (50 mg/kg/day i.p. at ZT12 for 7 consecutive days). The day after the last EdU administration, the animals were sacrificed and the tissue was processed as described above. The sections were air-dried at room temperature, then rehydrated with PBS for 10 min before incubation with EdU reaction cocktail. After rinsing, the sections were counterstained with a fluorescence nuclear stain (ToPro, Life Technologies, Stockholm, Sweden) for 5 min at room temperature, then mounted with fluorescence mounting medium (Dako, Golstrup, Denmark).

Maturation of newly generated neurons was assessed by counting doublecortin (DCX)-positive neuroblasts throughout the granule cell layer of DG. The DCX staining was performed following a standard sandwich immunohistochemistry protocol, as described herein.

The cell counting was performed in a stereological design on vertical sections. The total number of cells was estimated by multiplying the number of counted cells with the inverse sampling fraction.

Glucocorticoid receptor expression is enriched in the hippocampal area, and depression is associated with decreased GR expression, and prenatal exposure to DEX has been shown to decrease the hippocampal expression of GR. The GR labeling was performed using a standard sandwich immunohistochemistry protocol, as described above. The expression of GR was estimated by measuring the fluorescence intensity in the DG area relative to background fluorescence. The intensity of the positive signal was estimated in the granule cell layer (i.e., the area where the expression of GR is expected to occur in the cell bodies; manually delineated), and the background intensity was estimated in the molecular and polymorph layers of the DG. The GR labeling was estimated using the same sampling scheme as above, and the values were averaged for each mouse before comparing the groups.

Corticosterone Metabolites in Feces

The circadian pattern of GC secretion at 12 mo was investigated using a minimally invasive approach. To this end, spontaneous fecal boli were collected between ZT1-2 and ZT12-14 (i.e., immediately after the transition between the light and dark phases of the LD cycle). The feces were collected in sterile Eppendorf tubes and stored at −80° C. until further processing. Samples from each mouse were collected on two occasions (7 day interval between samplings) and the measurements for each mouse were averaged before analysing the differences across the LD cycle. The concentration of corticosterone metabolites in dry fecal extracts was measured by enzyme immunoassay according to manufacturer's instructions (DetectX™, Arbor Assays, Ann Arbor, Mass., USA).

Analysis of Clock Gene Expression in the Hippocampus

The clock genes display circadian patterns of expression throughout the brain and have the same period as the central pacemaker—the suprachiasmatic nucleus (SCN). In the hippocampus clock genes regulate neurogenesis, and the circadian fluctuations in expression are synchronised by circulating GC. The expression of clock genes was investigated in hippocampi harvested from male mice aged 3 mo (N=4/group) maintained in a 12 h:12 h LD cycle (light intensity 200 lx) for at least 7 LD cycles before sampling. The mice (2 mice/cage) were killed at ZT2 and ZT12 (i.e., 2 h after the beginning of, and at the end of the light phase, respectively) by an overdose of anesthetic (sodium pentobarbital, 150 mg/kg). The blood was removed by transcardial perfusion with ice-cold buffered saline. The hippocampus was quickly dissected on ice and stored at −80° C. until processing. The relative expression of clock genes (Clock, Bmal1, Per1/2, and RevErb-α) was assessed by quantitative real-time PCR with GAPDH as housekeeping gene, as described below.

RNA Extraction, cDNA Synthesis, and PCR Amplification

The RNA was extracted using the TRI™ Reagent (Sigma-Aldrich, Germany) as instructed by the manufacturer. The quality of the extracted RNA was checked using a NanoDrop™ 1000 UV spectrophotometer (Thermo Scientific, Wilmington, Del., USA). cDNA was prepared using a Superscript II first strand cDNA synthesis kit (Invitrogen Inc., Carlsbad, Calif., USA) starting from 2 μg total RNA and 0.5 μg oligo-dT primers, as instructed by the manufacturer. PCR amplification reactions were performed using 0.5 μl cDNA and SYBR® Green PCR Master Mix (Applied Biosystems, Life Technologies Corp., Warrington, UK) and 0.2 µM forward and reverse primers (total reaction volume adjusted to 12.5 µl with DNAse- and RNAse-free water) in a 7500 Fast Real-Time PCR System (Applied Biosystems) running 7500 software version 2.05. The negative control reactions contained water instead of cDNA template. The primer sequences are listed in Table 2. The PCR cyclic amplification was performed for 1 min at 60° C. for 45 cycles. The specificity of the amplification was checked by inspection of the melting curve and by electrophoresis in 2% agarose gel. The relative expression regulation was calculated as [illegible], with GAPDH as housekeeping gene. All amplification reactions were run in technical duplicates, and all experiments were repeated 3 times.

Analysis of Homecage Activity

The spontaneous activity of mice aged 1, 3, 5, and 12 mo (N=7-8/group) was recorded using the TraffiCage™ system (NewBehavior, Zurich, Switzerland). Briefly, the system consists of an array of radio frequency (RF) antennas placed under the cage with group-housed, freely moving mice. The antennas read the RFID tags and provide an approximate location of each animal with a time resolution of 20 ms. The time interval during which an animal is detected constantly by the same antenna is defined as a "visit." When an animal changes location enough to be detected by another antenna, a new visit is recorded. Each visit is described by the start time and duration. For long recordings, the number of visits is virtually equal to the number of transitions, and can be used as activity count. The time series of visits are exported as ASCII files and analysed using custom routines developed in Matlab™ R2013b (The MathWorks™, Natick, Md., USA).

The mice were housed in a climate-controlled, isolated room for a period of 6 to 7 weeks, with minimal interactions with human experimenters (except for changing the cage and to replenish food and water, which occurred at random times throughout the experiment). The synchronisation of activity monitoring with the LD cycle was ensured by using a remote control device (TellStick™, Telldus Technologies AB, Lund, Sweden) operated by the computer running TraffiCage™ control software. To minimize the effects of novelty and possible interference from circadian rhythm entrainment, the baseline measurements were derived based on 3 LD cycles after an acclimation period of at least 3 LD cycles. The mice were then exposed to constant darkness (DD) for 336 h (equivalent to 14 LD cycles). The free-running period is shorter than 24 h in young controls, which results in a large-enough phase advance (about 6 h at the end of DD period) to require circadian re-entrainment. The behavior in DD conditions was analysed over the last 72 h of recording in DD, and the effects of resetting the circadian rhythm were analysed during the first 3 LD cycles immediately upon resuming the LD cycle.

The analysis of circadian rhythmicity consisted of rhythmometry by means of cosinor analysis. The period of spontaneous activity was estimated as the highest peak in the $\chi^2$ periodogram between 20 and 25 h with 5 min resolution. We next analysed spontaneous activity by detrended fluctuation analysis (DFA). The method is based on linear regression analysis of the residual variance of the time series against the time scale used for detrending on double-logarithmic plots. The slope of a linear regression in double-logarithmic plot translates into a scaling exponent, and describes the long-term autocorrelation patterns embedded in the time series. Scaling exponent values around 0.5 are characteristic for random fluctuations; values above 0.5 indicate positively correlated long-range fluctuations; values close to 1 suggest strong underlying regularity; and values between 0.5 and 1 characterize complex timeseries with fractal-like patterned irregularity. The scaling exponent in healthy, freely moving rodents and humans is around 0.8, and the loss of patterned irregularity has been suggested to be a hallmark of disease.

Statistical Analyses

All statistical analyses were performed in Statistica™ version 12 (Statsoft Scandinavia, Uppsala, Sweden). Unless otherwise specified, simple, factorial, or repeated measures ANOVA models were used, followed by contrast analysis. The results are shown as average and standard error of the mean.

Results

Male Mice Exposed to DEX Prenatally Display Depression-Like Behavior that is not Reversed by Chronic Antidepressant Treatment Male offspring were tested in the FST at several ages, and it was found that DEX-exposed mice show increased immobility time at 12 mo, but not earlier (FIG. 1A). The depression-like phenotype was reconfirmed in the tail suspension test performed on mice aged 12 mo (FIG. 1B). The mice were then treated with FLX dissolved in drinking water (80 mg/L) for 21 days before repeating the test and it was found that the immobility time was not altered in DEX-exposed mice, but decreased in controls (FIG. 1A).

Depression has been associated with impaired neurogenesis. Moreover, neurogenesis restoration is required for the antidepressant effect of chronic FLX treatment. Studies were conducted to investigate whether the depression-like behavior in DEX-exposed mice at 12 mo was associated with impaired neurogenesis, and it was found that DEX-exposed mice had a lower number of EdU-positive cells in the SGZ and less DCX-positive cells in the granular layer of the dentate gyrus (FIGS. 1C, D). In agreement with the behavioral data, FLX treatment did not have any significant effect on neurogenesis in DEX-exposed mice. In agreement with earlier reports, FLX decreased the number of DCX+ cells in middle-aged controls.

Prenatal exposure to DEX has been shown to decrease the hippocampal expression of GR. The expression of GR in the hippocampal region was examined and it was found that 12 mo-old DEX-exposed mice displayed significantly lower GR signal intensity throughout the hippocampus, particularly in the DG (FIG. 10E and the CA3 region (not shown)).

The circadian fluctuations in GC secretion were also assessed and it was found that DEX-exposed mice had lower levels of corticosterone metabolites in the feces and did not show significant circadian fluctuations (FIG. 1F).

DEX-Exposed Mice Display Alterations in Circadian Rhythms that Precede Depression-Like Behavior To investigate the circadian rhythms, spontaneous activity in the homecage was monitored over extended periods of time. After recording the baseline activity (in the context of an already entrained LD cycle), the mice were challenged by exposing them to continuous darkness (DD) for 14 days. Upon resuming the LD cycle, the phase of the internal clock was being reset by the environmental light. Therefore the comparison between circadian rhythmicity before and after the DD period (i.e., baseline vs. forced synchronisation) provides an estimation of the dependence of the circadian rhythms on environmental cues. The circadian rhythmicity in LD cycle was investigated by means of cosinor analysis. The amplitude of the fitted function estimates the difference between the maximum and minimum activity (i.e., the bias towards moving more during the dark vs. the light phase of the LD cycle). The forced synchronisation of the circadian rhythm induced by resuming the LD cycle resulted in increased amplitude as compared to baseline, as seen in young controls. The DEX-exposed mice had larger amplitude at baseline, and showed no significant difference between baseline and forced synchronisation (FIG. 2A). This suggests that the effect of ambient light in driving the circadian rhythms was stronger in DEX-exposed mice.

Figure 2B:
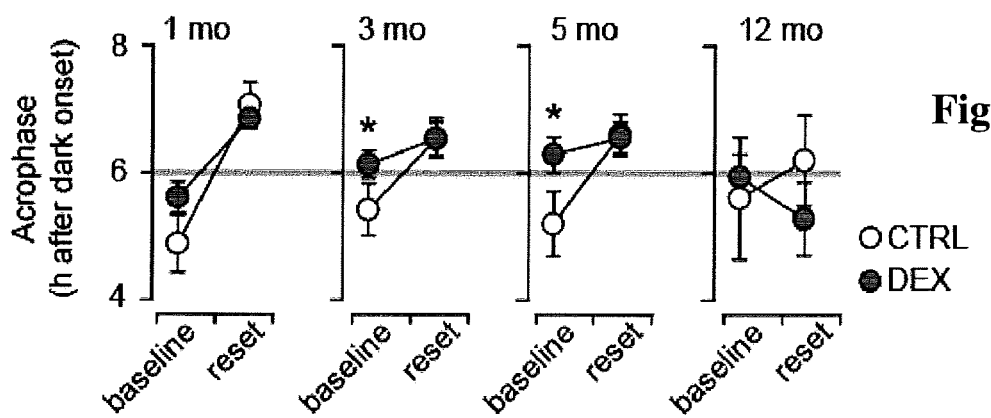

To further investigate the strength of the pacemaker effect of ambient light, the acrophase of the circadian rhythm (i.e., the location of the peak of activity in relation to the onset of the active phase of the LD cycle) was analysed. The acrophase occurs before ZT18 in normal animals that had been entrained in a 12:12 h LD cycle by anticipation of phase change (i.e., the animals become active before, and gradually cease the spontaneous activity before the offset of the dark phase). In contrast, an acrophase very close to, or lagging behind the middle of the dark phase (i.e., ZT18) occurs during forced synchronisation, when the animals become active after the onset, and cease all activity after the offset of the dark phase. Documentation could be done of the phase-shift anticipation at baseline and the synchronisation-induced lag in DEX-exposed mice only at 1 mo, while this pattern was consistently present in young (3-5 mo old) controls (FIG. 2B). Instead, the acrophase did not vary between baseline and forced synchronisation in DEX-exposed mice aged 3 mo and older. This suggests that the LD cycle had a stronger effect in driving the circadian rhythm of spontaneous activity, almost overriding the internal clock in DEX-exposed animals.

Figure 2C:
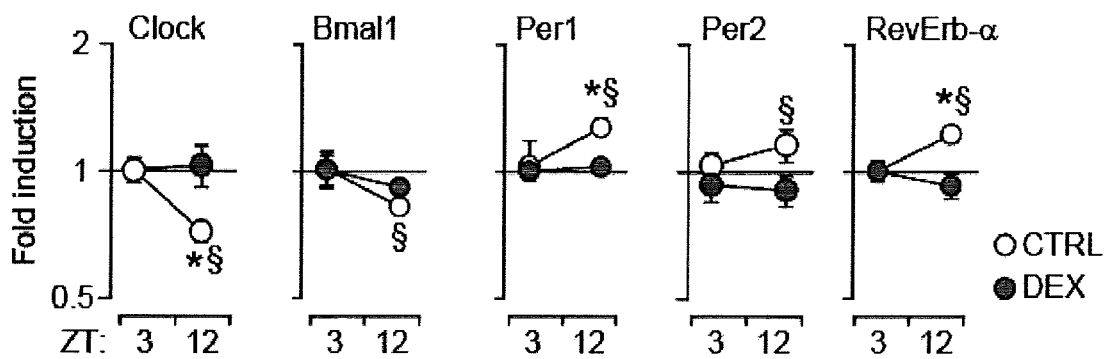

To further investigate the circadian clock function, the circadian fluctuations of gene expression were analysed for selected genes in the hippocampus at 3 mo, corresponding to the first documentation of altered circadian rhythms in DEX-exposed mice. It was found that the circadian oscillations in Clock, Bmal1, Per1, Per2, as well as in the master regulator Rev-Erb α, are blunted in DEX-exposed mice (FIG. 2C).

Altered Pattern of Spontaneous Activity in DEX-Exposed Mice

Figure 3A:
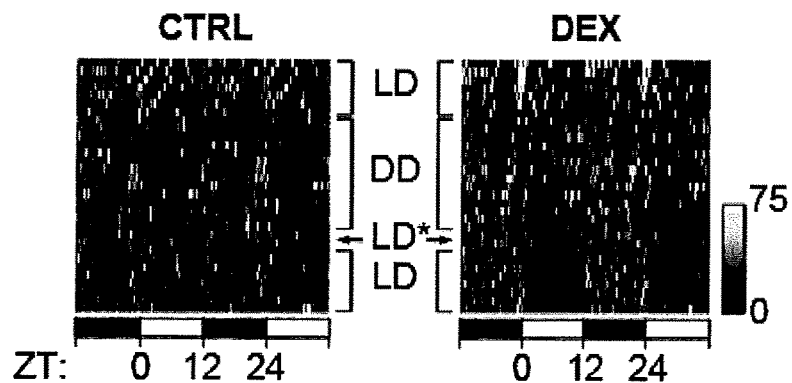
FIGS. 3A-3C. Alterations in spontaneous activity in DEX-exposed mice.
Figure 3B:
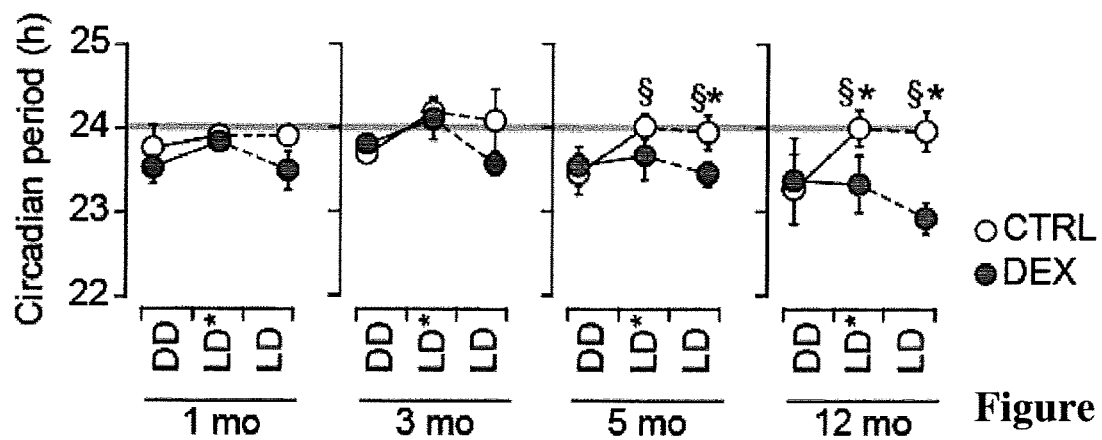
Figure 3C:
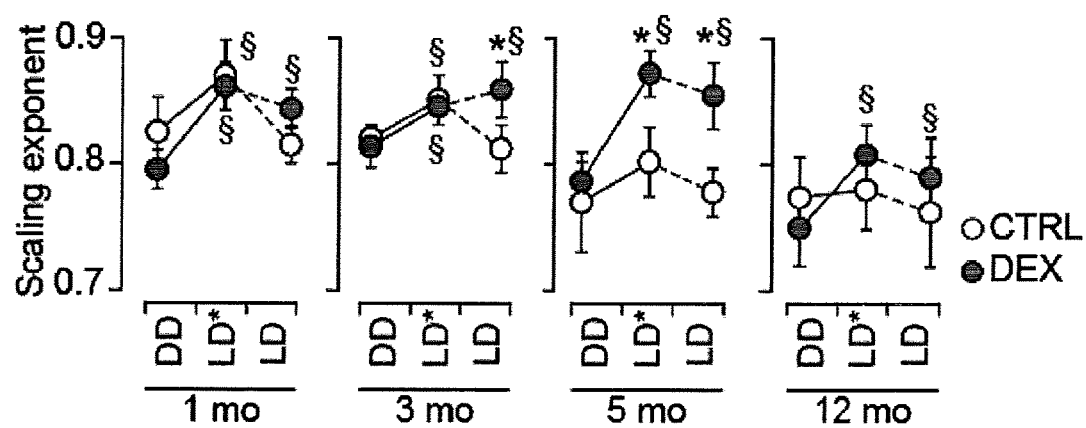

Next we performed an in-depth analysis of rhythmicity and regularity of spontaneous activity in the homecage. To this end the scaling exponent and the internal period of spontaneous activity were estimated. The internal period is shorter than 24 h in young animals, and this can be visualized as continuous phase-advance during DD (FIG. 3A). Circadian entrainment implies that the synchronised oscillation is self-sustained, and has a period similar to that of the light-dark cycle. Forced synchronisation induced circadian re-entraining in both controls and DEX-exposed mice, and the circadian period was close to 24 h at young ages (FIG. 3B). However, in young DEX-exposed animals during steady entrainment the circadian period displayed a tendency to deviate from 24 h, and the difference became significant in steady entrainment at the age of 5 months (FIG. 3B). Moreover, at 12 months, circadian entrainment failed in DEX-exposed mice even during forced synchronisation, and the circadian period did not vary between free-running, forced synchronisation, and steady entrainment (FIG. 3B). The activity of the SCN maintains the complex pattern of spontaneous activity regardless of the environmental conditions, and the scaling exponent did not vary between LD (baseline) and DD in healthy controls (FIG. 3C). In free-running conditions (DD), DEX-exposed mice had similar scaling exponent as controls. However, DEX-exposed mice displayed significant fluctuations in scaling exponent between free-running and circadian entrainment conditions at all ages investigated (FIG. 3C). This indicates that the SCN function is largely preserved in DEX-exposed mice. However, the sustained increase in scaling exponent under steady entrainment by constant LD cycle in DEX-exposed mice (FIG. 3C) suggests alterations in circadian entrainment. This is further supported by the shorter circadian period found in 12 months old DEX-exposed mice under constant steady entrainment conditions (FIG. 3B). Taken together, these findings indicate that circadian entrainment fails in DEX-exposed mice at 12 months of age, when depression-like behavior was documented.

Example 2

In Vitro Assay Using Primary Mouse Cells
Materials and Methods
Primary Fibroblast Cultures from Adult Mice Tissue samples (~0.25 cm$^2$) were harvested from the ear of adult (6 mo) control and DEX-exposed mice under terminal anesthesia. The tissue was rinsed in Hank's Balanced Salt Solution (HBSS) (Life Technologies Europe BV, Stockholm, Sweden), then minced with sterile razor blade into Collagenase (Type XI-S) (Sigma-Aldrich, Sweden) (30 min at 37° C.). After digestion, 3 ml of DMEM Medium (Life Technologies) supplemented with 10% Fetal Bovine Serum and 1% Penicillin/Streptomycin (Life Technologies) was added to a 6 cm plate and the samples were incubated at 37° C. for at least 6 days. After passaging (0.05% Trypsin-EDTA; Invitrogen), the cells were plated in 12 multi-well plates in MEF medium (DMEM Medium+10% FBS+1% pen/strep) at a density of at least 50 k/cm$^2$. After 24 h, the expression of clock genes was synchronised by adding DEX to a final concentration of 1 µM to the culture medium. The cells were then collected between 6 and 36 h after synchronisation. The relative expression of Bmal1 was assessed by qPCR with Gapdh as housekeeping gene as described in Example 1 (Table 2: SEQ ID NO 5 and 6, and 1 5 and 2, respectively).

All fibroblasts express functional molecular clock machinery, but its parameters differ slightly among cells. Therefore, while oscillations in clock gene expression can be documented in individual cells, such oscillations can only be detected at population level (by qPCR or using reporter systems) after synchronisation using DEX, serum shock, or medium change.

Results

Figure 5:
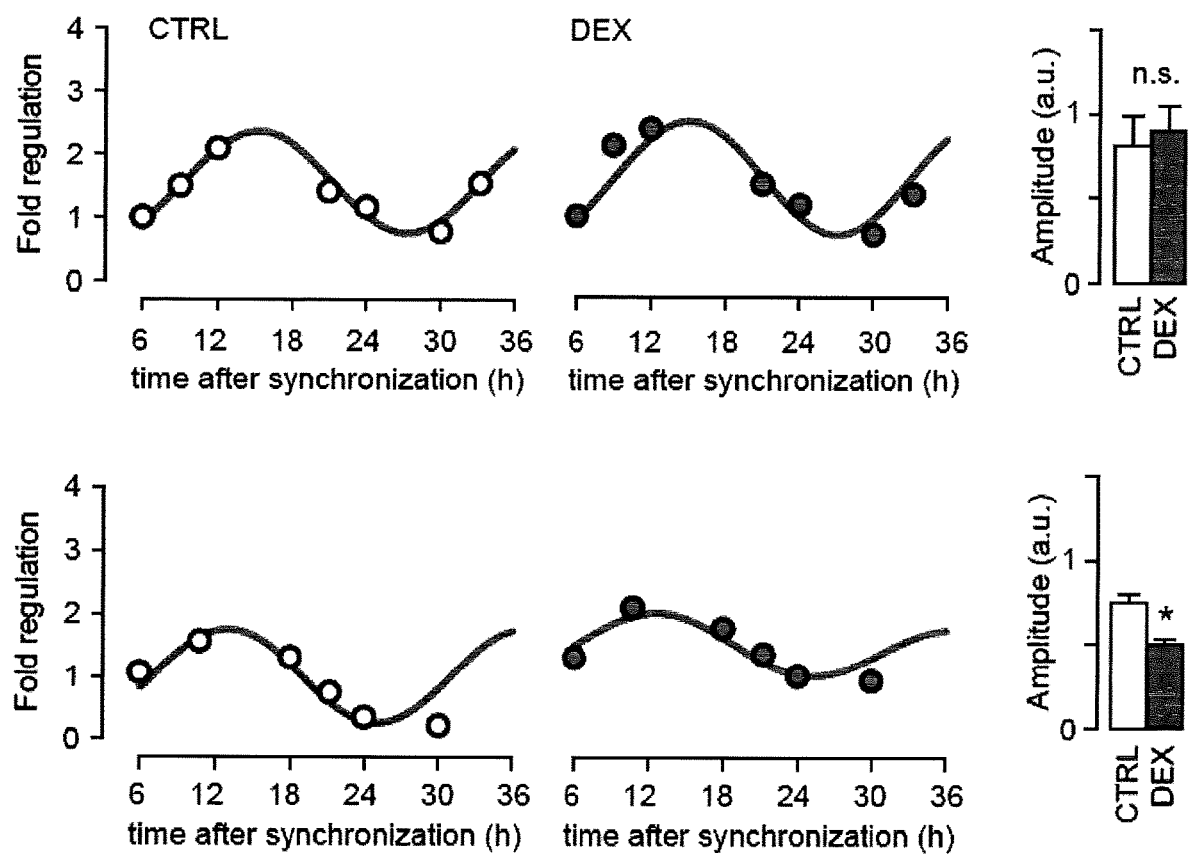
FIG. 5. Expression of Bmal1 in cultured fibroblasts. At the age of 1.5 mo (top panel), there were significant differences between DEX-exposed animals and controls. In contrast, at the age of 6 mo (bottom panel), fibroblasts isolated from DEX-exposed mice displayed attenuated oscillations in Bmal1 expression. It is interesting to note that DEX-exposed animals aged 6 mo, but not 1.5 mo also displayed alterations in circadian entrainment.

Circadian Rhythms are Attenuated in Primary Skin Fibroblasts Derived from DEX-Exposed Mice Skin fibroblasts express functional molecular clock machinery and the circadian oscillations in clock gene expression maintain to a large extent the features of circadian rhythms in the central clock. In addition, circadian entrainment (or synchronisation of self-sustained oscillations and ability to reset the phase) is preserved and can be studied in cultured fibroblasts. We therefore investigated the expression of clock genes in fibroblasts isolated from controls and DEX-exposed mice aged 1.5 and 6 mo (FIG. 5). The cells were harvested at different time points after synchronisation and the oscillations in gene expression were investigated by cosinor rhythmometry. Bmal1 was selected for analysis based on the central role it plays in the molecular clock machinery. Fibroblasts isolated from DEX-exposed mice aged 1.5 months displayed similar oscillations in clock gene expression as the control mice (FIG. 5, top panel). In contrast, fibroblasts isolated from DEX-exposed mice aged 6 mo displayed attenuated oscillations in Bmal1 expression (FIG. 5, bottom panel), consistent with the alterations in circadian entrainment we observed in spontaneous activity (FIGS. 2 and 3). In conclusion, we have shown that the amplitude of oscillations in Bmal1 expression in cultured fibroblasts was decreased in DEX-exposed mice, consistent with the alterations in circadian entrainment observed in their spontaneous activity and that the alterations can be detected before the onset of depression-like behavior, concomitantly with the altered circadian rhythmicity in steady entrainment.

Accordingly, the present invention provides a method of determining alterations in circadian rhythm, from measuring the expression of clock genes, using primary cells, for instance fibroblasts from skin biopsies comprising the following steps:

1) obtaining a sample of primary cells from a subject, such as skin fibroblasts and establishing the cells in culture;
2) culturing the sample for a period of time (e.g., until the cells are of sufficient number for further analysis). Once the cells are close to or have reached confluence, for example are at 70, 80, 90, 100% confluence;
3) synchronising the expression of the clock genes in the sample using exposure to a dose of 0.01-10 μM of dexamethasone, for example, 1 μM dexamethasone for a period of time ranging from about 1 to about 60 minutes, for example, 30 minutes;
4) measuring the expression of one or more clock genes, which can be, but is not limited to Clock, Bmal, Per and/or Rev-Erb, by means of an amplification reaction such as polymerase chain reaction (PCR), including qPCR from serial samples (e.g., samples are collected at multiple time points after synchronisation, for example, a period of time of about 1 to about 48 hours, for example, 6 to 36 hours;
5) analysing the circadian rhythm parameters (period, amplitude and phase) of the series of samples of step 4 and comparing the parameters obtained with the circadian rhythm parameters obtained from a control sample (e.g., a subject who does not have or is not suspected of having depression, or a neuropsychiatric disorder).

Example 3

Reporter Gene Assay Using Primary Mouse Cells

Prior to acquiring a biological sample, such as a skin biopsy, from an animal, for instance, a mouse, the subject can be monitored for a period of time in order to estimate the intrinsic rhythmicity of spontaneous activity. The biological sample, including, e.g., a skin biopsy can be collected either once, in duplicate or triplicate numbers, in circular patches ranging from 1-5 mm in diameter, for example, 2 mm and can be collected anywhere, including from the ear.

A subsequent method of estimating clock gene expression, or alterations thereof, using mouse primary cells, such as fibroblasts from skin biopsies can use the following steps:

1) infecting primary cells, such as fibroblasts, with a lentivirus comprising the promoter of one or more clock genes, for example, Clock, Bmal, Per and Rev Erb and a reporter gene, for example, firefly luciferase;
2) after a period of incubation, up to 7 days post-lentivirus infection, for example 5 days, synchronising the expression of clock genes in culture using exposure to a dose of 0.01-10 μM of dexamethasone, for example, 0.1 or 1 μM dexamethasone for a period of time ranging from 1-60 minutes, for example, 30 minutes. The bioluminescence signal intensity can be measured in the presence of 0.01 to 10 mM luciferin, for example, 0.1 mM luciferin, and can be recorded for 1-120 hours or for 1, 2 or 3 weeks, for example, 60 or 72 hours. The characteristics of fluctuations in bioluminescence signal intensity (period, amplitude and phase) can be estimated by means of cosinor analysis before;
3) administering a secondary pulse of 0.01-10 μM of dexamethasone, for example, 0.1 or 1 μM Dex, to induce a phase shift/advance (of 6-18 hours, including 12 hours) and bioluminescence signal intensity can be recorded in the presence of 0.01 to 10 mM luciferin, for example, 0.1 mM luciferin, for an additional 1-96 hours, for example, 60 or 72 hours. The characteristics of fluctuations in bioluminescence signal intensity (period, amplitude and phase) can be estimated by means of cosinor analysis before;
4) determining expression of clock genes, or alterations thereof.

Example 4

Combined Actigraphy and Reporter Gene Assay Using Primary Human Cells

Prior to, or following, acquiring a biological sample, such as a skin biopsy from a human subject, the subject may wear an actigraphy device (e.g., Philips™ ActiCal™ or Acti-Watch™) for a period of time, for example, including, but not limited to 5-7 days, in order to estimate the intrinsic rhythmicity of spontaneous activity as follows:

1. The actigraphy device can be worn attached to a wrist band and record the movements of the arm by means of an embedded accelerometer. The raw activity data can be exported and analysed (for instance in Matlab™ environment) using custom implementations of publicly available algorithms, such as the following algorithms:

a) cosinor analysis; the output includes acrophase (e.g., location of the main cluster of activity in relation to light phase/clock time), amplitude of fluctuations in amount of activity and mesor (e.g., average hourly activity and relevant only in relation to amplitude). Wherein, low amplitude and acrophase not synchronised with the light phase (e.g., activity biased towards the evening or towards the morning) can indicate that the internal clock is out of phase compared to the light-dark cycle and can point to a higher likelihood of developing depression. Alternatively, weak rhythmicity (e.g., very low amplitude or flat distribution of activity throughout the day) can indicate low central clock drive;

b) unbiased periodogram (for instance chi-square) analysis, wherein, a circadian period considerably different from 24 h (most often shorter) can indicate a greater risk of a subject having/developing neuropsychiatric disorders. In addition, prominent peaks at shorter periods can indicate a tendency to engage in rigid behavioral loops; and c) detrended fluctuation analysis, which is a proxy measure of how strong the drive of the central clock is and the output parameter, or scaling exponent, should be around 0.8 in healthy controls. Higher values can indicate strong underlying rhythms (such as rigid entrainment of circadian rhythms, or repetitive behavioral sequences) and low values can indicate random and unstructured activity patterns.

Therefore, the results from the former actigraphy analyses can be used to derive a behavioral profile in order to estimate the risk of a subject developing a neuropsychiatric disorder (e.g., depression, bipolar disorder, etc.).

Subsequently, or in parallel with performing actigraphy, a biological sample, such as a skin biopsy can be collected from the subject of the actigraphy recordings either once, in duplicate or triplicate numbers in circular patches ranging from 1-5 mm in diameter or in strips, for example, 5 mm long and 2 mm wide. The former skin biopsies can be collected anywhere, including from the arm and more specifically from the anterior aspect of the forearm, or the medial aspect of the arm, before a method of determining clock gene expression, or alterations thereof, using human primary cells, such as fibroblasts from skin biopsies can be used in the following steps:

1) infecting primary cells, such as fibroblasts, with a lentivirus containing the promoter of one or more clock genes, for example, Clock, Bmal, Per and/or Rev-Erb and a reporter gene, for example firefly luciferase;

2) after a period of incubation, up to 7 days post-lentivirus infection, for example 5 days, synchronising the expression of clock genes in culture using exposure to a dose of 0.01-10 µM of dexamethasone, for example, 0.1 or 1 µM dexamethasone for a period of time ranging from 1-60 minutes, for example, 30 minutes. The bioluminescence signal intensity can be measured in the presence of 0.01 to 10 mM luciferin, for example, 0.1 mM luciferin, and can be recorded for 1-120 hours or for 1, 2 or 3 weeks, for example, 60 or 72 hours. The characteristics of fluctuations in bioluminescence signal intensity (period, amplitude and phase) can be estimated by means of cosinor analysis before;

3) administering a secondary pulse of 0.01-10 µM of dexamethasone, for example, 0.1 or 1 µM Dex, to induce a phase shift/advance (of 6-18 hours, including 12 hours) and bioluminescence signal intensity can be recorded in the presence of 0.01 to 10 mM luciferin, for example, 0.1 mM luciferin, for an additional 1-96 hours, for example, 60 or 72 hours. The characteristics of fluctuations in bioluminescence signal intensity (period, amplitude and phase), as illustrated in FIG. 4, can be estimated by means of cosinor analysis, before; 4) determining the expression of clock genes, or alterations thereof.

The behavioral profile data obtained through actigraphy can subsequently be used and/or analysed in combination with results obtained from the biological assays of this invention to (i) estimate the risk of a subject developing/having a neuropsychiatric disorder (e.g., depression, bipolar disorder, etc.), (ii) determine pharmacoresponse of a subject to a psychotropic drug or (iii) monitor/guide the treatment using a psychotropic drug in a subject.

An example of how results of actigraphy recordings can be combined with results from the biological assay comprises firstly, designating a subject as positive or negative for an altered circadian rhythm, as compared to a healthy control (e.g., a subject that is not suspected of suffering from a neuropsychiatric disorder) using a cut-off value or profile from analysing said subjects actigraph recordings as described herein and secondly, designating a subject as positive or negative for an altered circadian rhythm, as compared to a healthy control (e.g., a subject that is not suspected of suffering from a neuropsychiatric disorder) using a cut-off value or profile from measuring said subject's expression of clock genes as described herein.

The subject may subsequently be referred to as, for instance, double positive if the subject scored positive in both the actigraphy and the biological assay. The designation of double positive, or double negative, can provide additional certainty in terms of diagnosing a subject to be at increased risk of developing/having a neuropsychiatric disorder, or not being at risk of developing/having a neuropsychiatric disorder, respectively.

Example 5

Actigraphy in Human Subjects and Animals

Actigraphs (ActiCal™, Philips Respironics™, Koninklijke Philips, The Netherlands) were worn continuously by volunteers for at least 5 consecutive days. The devices were attached to the wrist of the dominant arm by means of an adjustable wrist strap so that the device sits firmly, but comfortably and not too tight to hinder the blood flow to the hand. Wrist actigraphy is an established technique to assess activity in human subjects based on accelerometers embedded in a recording device to be worn on the wrist. It can therefore record all wrist movements for extended periods of time and can be used to assess the modulation of activity under the influence of multiple intrinsic and extrinsic factors (ranging from light-dark cycle to social interactions and meal times). However the scale invariance property measured by detrended fluctuation analysis implies that all modulation follows a similar pattern at multiple scales (from minutes to hours) and dysfunctions in circadian rhythm regulation (e.g., altered circadian entrainment) will have corresponding alterations at shorter scales (minutes). In actigraphy recordings this can be seen as lack of modulation of activity level during the active phase. The data in this experiment was recorded in 5 s epochs. After downloading using the proprietary serial communication device (ActiCal™ 3.1, Philips Respironics™) the raw data was exported as ASCII files and analysed using custom routines developed under Matlab™ (The MathWorks™, Natick, Mass., USA). The analyses included chi-square periodogram, cosinor, and detrended fluctuation analysis, as described in Example 4.

The DEX-exposed mouse model has been described in Example 1 and the mouse data is also illustrated in FIG. 3A.

Results

Figure 6A:
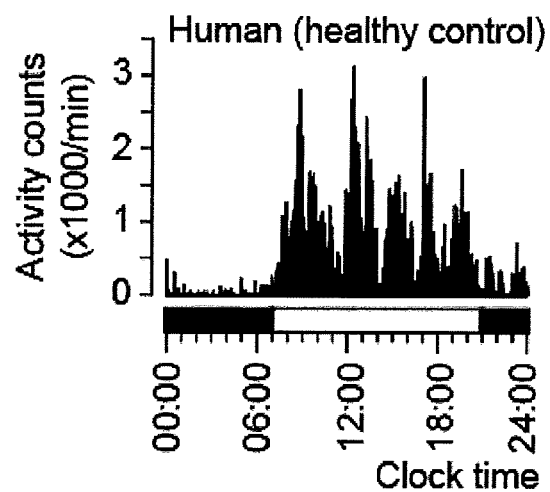
FIGS. 6A-6D. Actigraphy recordings in human subjects (FIGS. 6A, 6B), compared with experimental data recorded in mice (FIGS. 6C, 6D). The data is displayed so that the active phase (light for humans and dark for mice) is in the middle of the 24 h period. The absolute values of activity counts vary dramatically between human and mouse recordings due to differences in data acquisition methods. The healthy human subject (FIG. 6A) and the healthy (control) mouse (FIG. 6C) have distinct clusters of activity during the active phase and the activity levels vary smoothly around the transitions between active and inactive phases. In mice in particular (FIG. 6C), it was obvious that the activity started to increase ahead of the onset of the dark phase. In contrast, the subject with seasonal depression (FIG. 6B) and the DEX-exposed mouse, that eventually developed depression-like behavioral alterations, (FIG. 6D) displayed abrupt changes in level of activity in response to the onset and offset of active phase.
Figure 6B:
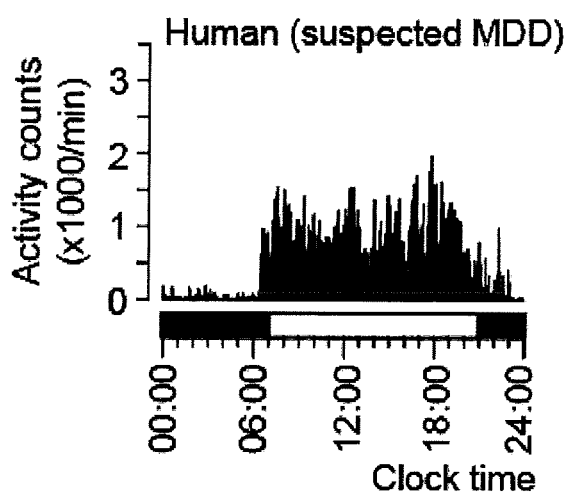
Figure 6C:
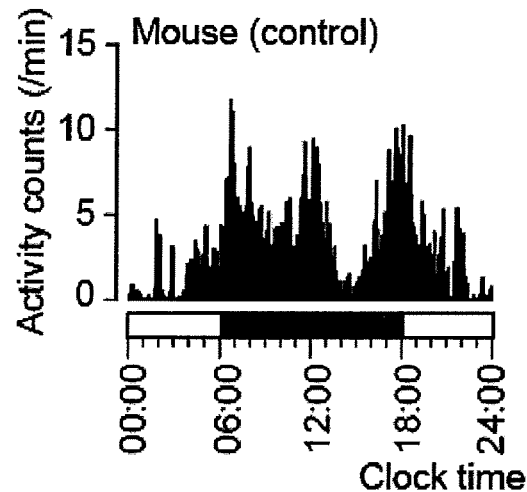
Figure 6D:
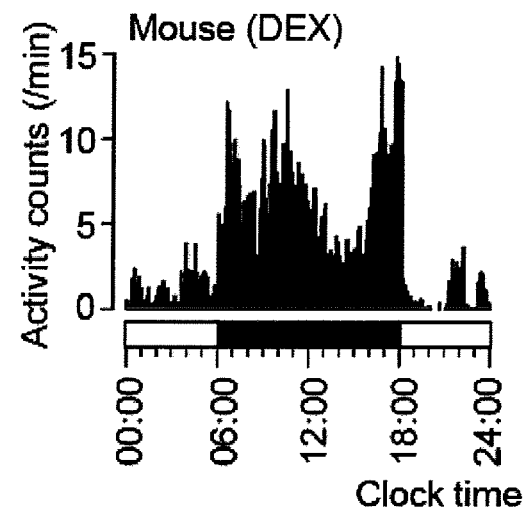

One of the volunteers was suffering from seasonal depression (as diagnosed by a medical doctor) and was suspected of also suffering from MDD. At the time of the actigraphy recording the former subject was not taking antidepressant medication. FIGS. 6A-6D depict the actigraphy activity in 5 min time bins averaged over 5 days of continuous recording for one healthy subject (FIG. 6A) and one subject suffering from seasonal depression and possibly also MDD (FIG. 6B). Visual inspection of the actigraphy recordings revealed striking differences in the distribution pattern, particularly during the active period. Of interest is the complex modulation of activity level during the active period, as well as the smooth transitions between the active and inactive phase in a healthy subject. In contrast, the subject with seasonal depression (FIG. 6B) displayed reduced modulation of activity during the active period and an abrupt transition from the resting to active state, particularly in the morning. The pattern of alterations described here is to a large extent similar to the alterations we found in our experimental model, which are described in EXAMPLE 1 (FIGS. 6C-D shows spontaneous activity recordings from one control—FIG. 6C—and one DEX-exposed mouse—FIG. 6D). The corresponding scaling coefficients are 0.80, 0.92, 0.82 and 0.88 for (A), (B), (C) and (D) respectively, which indicate more rigid fluctuations in (B) and (D) as compared to (A) and (C), respectively.

Based on these preliminary data, we propose that the failure to integrate the regular schedule into the intrinsic circadian rhythm can identify depressed subjects that will not respond to SSRI treatment. A possible further development of these observations is the design of a turnkey system to continuously record actigraphy data and run online analysis to continuously monitor the fluctuations in activity over periods of time ranging from minutes to hours/days. Specific alterations in the pattern of variation would presumably precede the onset of severe depressive episodes and can be used to issue a warning to both patients at risk of developing a depressive episode and/or a healthcare practitioner to take action in order to prevent/lessen the impact of such severe depression episodes.

Example 6

In Vitro Assay Using Primary Human Fibroblasts

A skin biopsy (about 5×2 mm) was collected from the internal aspect of the arm under sterile conditions after local anesthesia using EMLA patches (AstraZeneca, Sodertalje, Sweden). The wound was then covered with a sterile patch, and a small scar is formed typically within 6-12 h. The tissue sample was quickly transferred to ice-cold HBSS (Life Technologies Europe BV, Stockholm, Sweden) and minced with a sterile razor blade into Collagenase (Type XI-S) (Sigma-Aldrich, Sweden) (30 min at 37° C.). After digestion, 3 ml of DMEM Medium (Life Technologies) supplemented with 10 mM Hepes buffer, sodium pyruvate, non-essential amino acid mixture, glutamax, 20% Fetal Bovine Serum, and 1% Penicillin/Streptomycin (all supplements were from Life Technologies) was added to a 6 cm plate and the samples were incubated at 37° C. until the fibroblasts reached confluence (typically 3-4 weeks). The confluent fibroblast cultures were passaged (0.05% Trypsin-EDTA; Invitrogen) then plated in 12 multi-well plates at a density of at least 50 k/cm² in the same medium as used above. After 24 h, the expression of clock genes was synchronised by the addition of DEX to the culture medium to a final concentration of 1 µM. The cells were collected between 6 and 36 h after synchronisation. The relative mRNA expression of BMAL1, PER1 and PER2 (Table 2: SEQ ID NO 19 and 20) was assessed by qPCR with HP RT (Table 2: SEQ ID NO 13 and 14) as housekeeping gene. The qPCR procedure is described in Example 1.

Results

Figure 7:
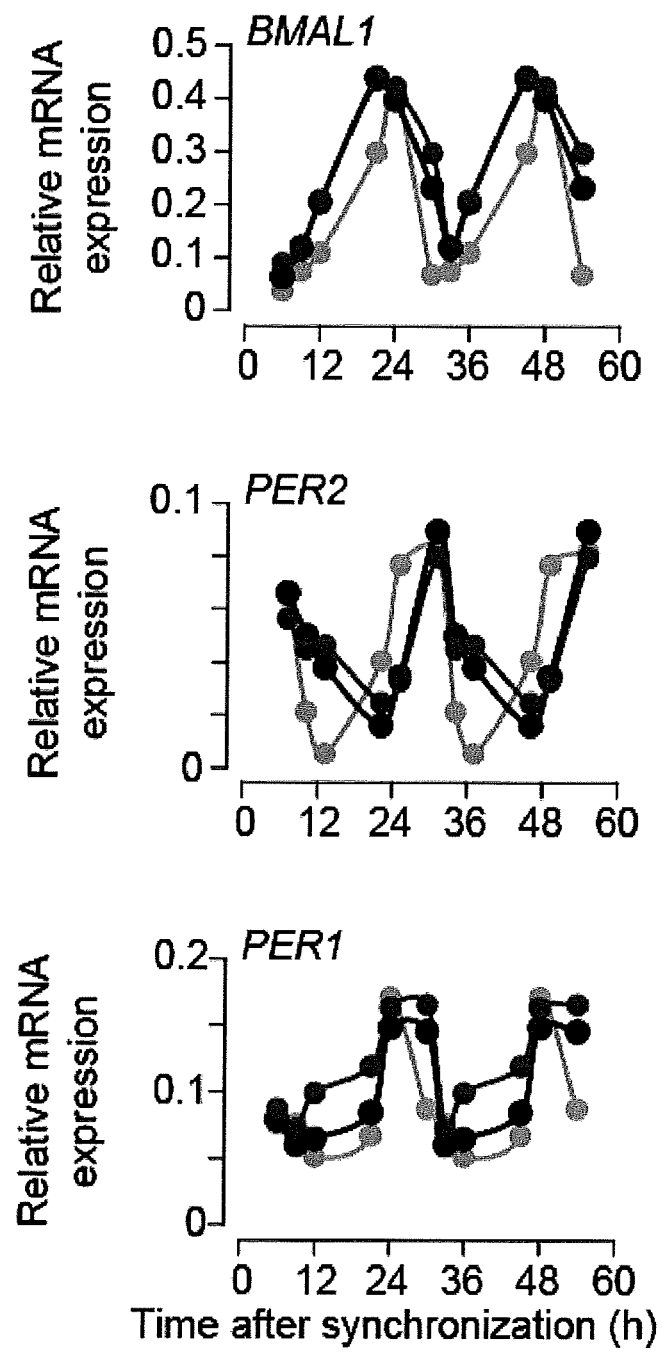
FIG. 7. Fluctuations in clock gene expression in human fibroblasts. Skin samples collected from healthy subjects; wherein the two different shades of grey identify the two subjects. The PCR sampling covers the first 36 h after DEX synchronisation, and is plotted twice for illustration purposes.

The mRNA expression of clock genes BMAL1 and PER1/2 in primary fibroblasts from three healthy subjects is shown in FIG. 7. The addition of DEX to the culture medium should induce a strong up-regulation of PER1, which suppresses the expression of BMAL (one of the main components of the positive arm of the feedback loop which induces expression of PER1/2), and thereby resets the molecular clock in all fibroblasts. The oscillations in mRNA expression for the selected clock genes have the same period (about 24 h), but their phases differ considerably. In particular mRNA expression for BMAL and PER1/2 vary in opposite directions (i.e. when BMAL increases, PER1/2 decrease and vice versa).

These results indicate that the assay developed in mouse models can be translated into clinical practice. The assay can be further be refined by using a reporter gene system (e.g., firefly luciferase with a clock gene promoter) delivered by means of lentiviral infection, as described in Example 4 (see (Brown et al. 2005)). We predict this will lead to bioluminescence recordings similar to those depicted in FIG. 4A.

These results indicate that the assay developed in mouse models can be translated into clinical practice. The assay can be further refined by using a reporter gene system (e.g., firefly luciferase with a clock gene promoter, for instance BMAL1) delivered by means of lentiviral infection, as described in Example 4 (see (Brown et al. 2005)). We predict this will lead to bioluminescence recordings similar to those depicted in FIG. 4A.

Example 7

Luciferase Reporter Gene Assay in Primary Mouse Cells

Materials and Methods

The generation of knock-in mice expressing firefly luciferase under the control of Per2 promoter (Per2::Luc) has been described previously (Yoo et al. 2004).

Tissue samples (about 0.25 cm²) were harvested from the ear of adult (6 mo) control and Dex-exposed mice under terminal anesthesia. The tissue was rinsed in Hank's Balanced Salt Solution (HBSS) (Life Technologies Europe BV, Stockholm, Sweden), then minced with sterile razor blade into Collagenase (Type XI-S) (Sigma-Aldrich, Sweden) (30 min at 37° C.). After digestion, 3 ml of DMEM Medium (Life Technologies) supplemented with 10% Fetal Bovine Serum and 1% Penicillin/Streptomycin (Life Technologies) was added to a 6 cm plate and the samples were incubated at 37° C. for at least 6 days. After passaging (0.05% Trypsin-EDTA; Invitrogen), the cells were plated in 12 multi-well plates in MEF medium (DMEM Medium+10% FBS+1% pen/strep) at a density of at least 50 k/cm². After 24 h, the cell culture medium was exchanged for air-buffered DMEM (D2902, Sigma-Aldrich, St Louis, Mo., USA)) supplemented with 1× B27 (20 mL of 50× B27 in 1 L; Invitrogen), 10 mM HEPES, Pen/Strep 25000 U/ug/L (Invitrogen), D-glucose 0.35% and NaHCO3 350 mg/L, and 0.1 mM luciferin (Promega, Madison, Wis., USA). The expression of clock genes was synchronised by adding DEX to the culture medium to a final concentration of 1 µM before covering the culture plates with glass coverslips made air-tight using silicone-based vacuum grease (Dow Corning Corp, USA). The culture dishes were immediately placed in a LumiCycle™ 32 system (ActiMetrics™, Wilmette, Ill., USA) to record the bioluminescence signal using photomultiplier tubes in photon count mode. The number of photons emitted by each culture dish was counted over 1 minute every 10 min (time resolution: 6 data points/h). The time series were further analyzed by means of cosinor analysis as described in Example 4.

Results

Figure 4A:
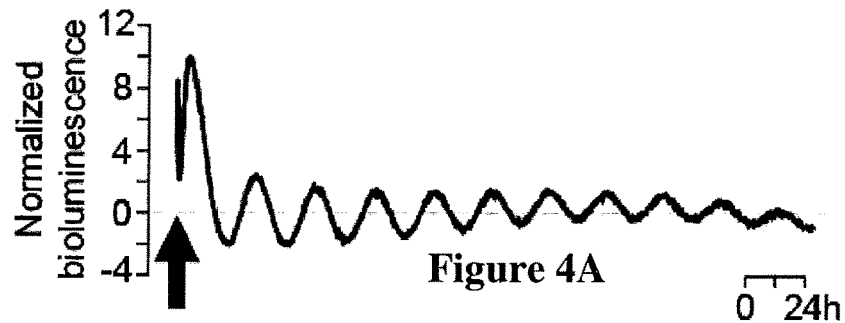
FIGS. 4A-4D. Circadian oscillations in clock gene expression. Reporter signal amplitude in cultured fibroblasts.
Figure 4B:
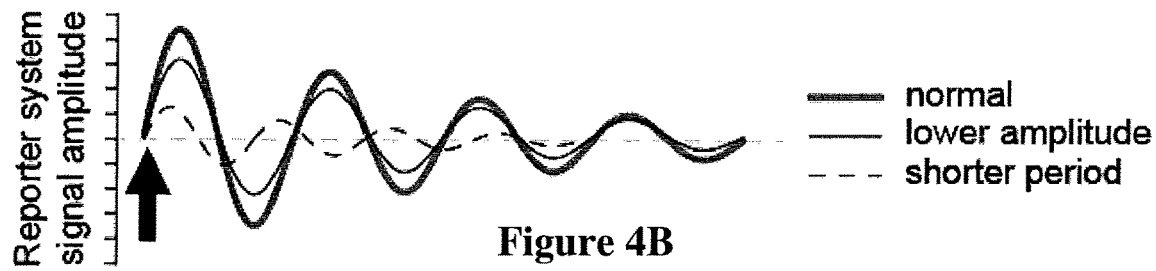
Figure 4C:
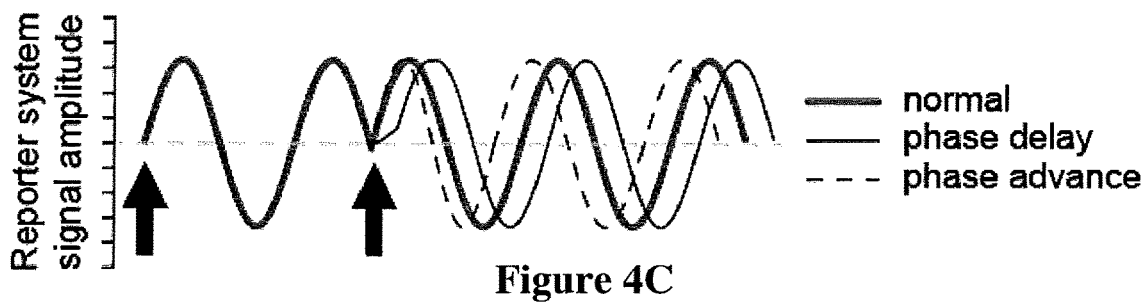
Figure 4D:
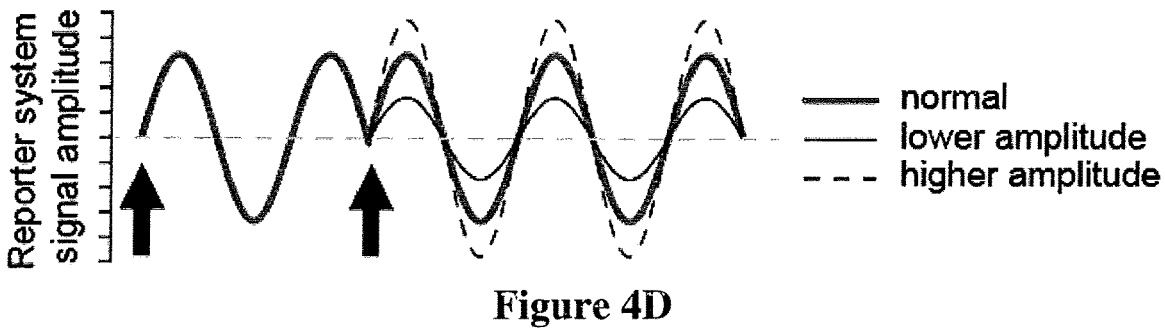

A representative trace is shown in FIG. 4A. Note that the oscillations are self-sustained and can be detected for as long as 10 days after the initial DEX synchronisation. Alterations in oscillations of bioluminescence signal intensity (FIG. 4B) reflect changes in molecular clock function. For example, lower amplitude, or the lack of phase reset immediately after resynchronisation indicate diminished response to entraining stimuli. A second administration of DEX would reset the molecular clock mechanism. Possible responses to resynchronisation are illustrated in FIG. 4C and FIG. 4D.

Example 8

In Vitro Reporter Assay Using Primary Human Fibroblasts in a Bipolar Patient

Materials and Methods

A skin biopsy (about 5×2 mm) was collected from the internal aspect of the arm under sterile conditions after local anesthesia using EMLA patches (AstraZeneca, Södertälje, Sweden). The wound was then covered with a sterile patch. The tissue sample was quickly transferred to ice-cold HBSS (Life Technologies Europe BV, Stockholm, Sweden) and minced with a sterile razor blade into Collagenase (Type XI-S) (Sigma-Aldrich, Sweden) (30 min at 37° C.). After digestion, 3 ml of DMEM Medium (Life Technologies) supplemented with 10 mM Hepes buffer, sodium pyruvate, non-essential amino acid mixture, glutamax, 20% Fetal Bovine Serum, and 1% Penicillin/Streptomycin (all supplements were from Life Technologies) was added to a 6 cm plate and the samples were incubated at 37° C. until the fibroblasts reached confluence (about 4 weeks). The cells were passaged (0.05% Trypsin-EDTA, Invitrogen; 10 min at 37° C.), then plated in 35 mm dishes at a density of about 25 k/cm2 (200.000 cells/dish) in human fibroblast medium (500 ml DMEM+glutamax (Life Technologies 61965-026), 5 ml 1 M HEPES buffer solution (Life Technologies Cat No. 15630-056), 10 ml 50× nonessential amino acid mixture (Life Technologies Cat No. 11130-036), 5 ml 100× sodium pyruvate (Life Technologies Cat No. 11360-039), 5 ml 100× penicillin/streptomycin (Life Technologies Cat No. 15140-122), 100 ml FBS (Life Technologies Cat No. 10270-106) supplemented with hexadimethrine bromide 18 µg/mL (Sigma-Aldrich Cat No. H9268).

Figure 8A:
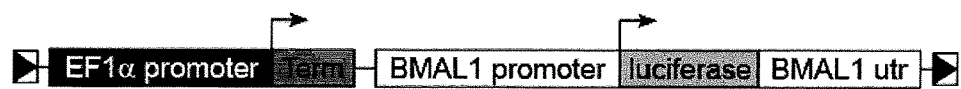
FIGS. 8A and 8B. Reporter construct for lentiviral luciferase expression vector (FIG. 8A) and illustrative example of altered oscillations of clock gene expression in response to a second pulse of DEX (FIG. 8B). The bioluminescence signal was recorded in primary skin fibroblasts after lentiviral delivery of a reporter system (depicted in (A)). The former skin samples were isolated from one healthy control (dark grey trace) and one subject with bipolar disorder (light grey trace). The photons were counted for 1 min every 10 min and are reported as average photon counts for each time point after normalisation by average subtraction. DEX was added directly to the culture medium (at the time points indicated by the two arrows) in order to synchronise and reset, respectively, the expression of clock genes. Note that a dramatic drop in bioluminescence signal intensity followed the second pulse of DEX occurs in the healthy control, but not in the subject with bipolar disorder.

Twenty minutes after plating, the cells were infected with a lentivirus encoding firefly luciferase driven by BMALI promoter using a multiplicity of infection (MOI) of 6. The reporter cassette consists of 1 kb of mouse Bmall upstream region and 53 nucleotides of exon 1, fused in-frame to the luciferase (Luc) coding region, and followed by 1 kb of Bmall 3' untranslated region. The Bmall:Luc reporter cassette is inserted downstream of an EF 1 a promoter and SV40 terminator in the pWPI vector ((Brown et al. 2005) as illustrated in FIG. 35 8A). The lentiviral particles were provided by Tebu-Bio (Ile-de-France, France). After 72 h, the medium was replaced with fresh human fibroblast medium. After an additional 4 days in culture (i.e., 7 days after infection), the culture medium was replaced with air-buffered DMEM (D2902, Sigma-Aldrich, St Louis, Mo., USA)) supplemented with IX B27 (20 mL of SOX B27 in 1 L; Invitrogen), 10 mM HEPES, Pen/Strep 25000 U/ug/L (Invitrogen), D-glucose 0.35% and $NaHCO_3$ 350 mg/L, and 0.1 mM luciferin (Promega, Madison, Wis., USA). The expression of clock genes was synchronised by adding DEX to the culture medium to a final concentration of 1 µM before covering the culture plates with glass coverslips made air-tight using silicone-based vacuum grease (Dow Corning Corp, USA). The culture dishes were immediately placed in a LumiCycle™ 32 system (ActiMetrics™, Wilmette, Ill., USA) to record the bioluminescence signal using photomultiplier tubes in photon count mode. The second pulse of DEX was administered 5 days after the first synchronization by direct addition to the culture medium to a final concentration of 1 µM. The culture dishes were re-placed in the LumiCycle™ system and the bioluminescence signal was recorded for an additional 24 h by recording. The number of photons emitted by each culture dish was counted over 1 minute every 10 min. The bio luminescence intensity was normalized by detrending (average subtraction).

Results

Figure 8B:
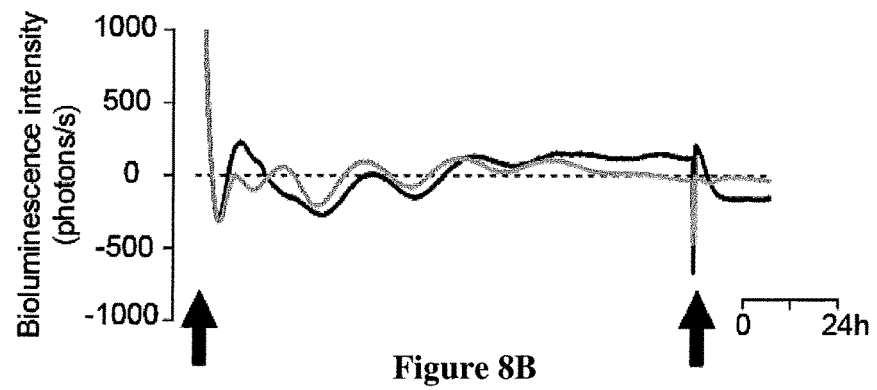

The first pulse of DEX was followed by self-sustained oscillations in BMAL1 promoter activation, as shown by the fluctuations in bioluminescence signal produced by the reporter system (FIG. 8B).

The amplitude of the oscillations decreased over time because the synchronization across the entire cell population was gradually lost. After the first synchronization, the period of oscillations was shorter in the subject with bipolar disorder than in the healthy control. Next, the second pulse of DEX was administered in order to resynchronise the expression of clock genes in the fibroblast culture. The mechanism of the molecular clock reset induced by the DEX pulse is presumed to be driven by up-regulation of PER1 expression (the promoter sequence of PER1 contains a GR binding domain and is activated by even very low concentrations of DEX, see (Reddy et al. 2012)), which in turn suppresses the expression of BMAL1. As expression of PER1 gradually decreases, a progressive increase in BMAL1 expression is seen and the oscillations in clock gene expression are resumed.

In the reporter system described herein, a pulse of DEX should be followed by a dramatic suppression of the bioluminescence signal, since the GR-driven up-regulation of PER1 expression is expected to suppress activation of the BMAL1 promoter. The former effect was obvious in the healthy control sample, while fibroblasts isolated from the subject with bipolar disorder displayed only a minor negative deflection after the second pulse of DEX. This suggests a defective response to GR activation, which could not have be inferred after the first pulse of DEX alone. Therefore, a possible interpretation in this case is that the subject with bipolar disorder has an impaired response to GR activation, which leads to desynchronised endogenous circadian rhythms.

All publications, patent applications, patents, patent publications, sequences identified by GenBank® Database accession numbers and/or SNP accession numbers, and other references cited herein are incorporated by reference in their entireties for the teachings relevant to the sentence and/or paragraph in which the reference is presented.

TABLE 1

| antigen | Manufacturer | Cat No. | dilution | incubation time |
|---|---|---|---|---|
| GR | Santa Cruz Biotechnology | GRH-300 | 1:500 | 72 h |
| DCX | Millipore Inc. | AB2253 | 1:1000 | overnight |

TABLE 2

| Primer | species | SEQ ID NO | Sequence |
|---|---|---|---|
| GAPDH | mouse | 1 | fw CAAGGCCGAGAATGGGAAG |
|  |  | 2 | rv GGCCTCACCCCATTTGATGT |
| Clock | mouse | 3 | fw GGCGTTGTTGATTGGACTAGG |
|  |  | 4 | rv GAATGGAGTCTCCAACACCCA |
| Bmal 1 | mouse | 5 | fw AACCTTCCCGCAGCTAACAG |
|  |  | 6 | rv AGTCCTCTTTGGGCCACCTT |
| Per 1 | mouse | 7 | fw CCAGATTGGTGGAGGTTACTGAG |
|  |  | 8 | rv GCGAGAGTCTTCTTGGAGCAGTA |
| Per 2 | mouse | 9 | fw AGAACGCGGATATGTTTGCTG |
|  |  | 10 | rv ATCTAAGCCGCTGCACACACT |
| Rev-Erb α | mouse | 11 | fw GGAACGGACCGTCACCTTT |
|  |  | 12 | rv TCCCCTGCTCCCATTGAGT |
| HPRT | human | 13 | fw ACCCCACGAAGTGTTGGATA |
|  |  | 14 | rv AAGCAGATGGCCACAGAACT |
| BMAL1 | human | 15 | Fw GCCGAATGATTGCTGAGGAA |
|  |  | 16 | Rv GGGAGGCGTACTCGTGATGT |
| PER1 | human | 17 | Fw TCTACATTTCGGAGCAGGCAGCCG |
|  |  | 18 | Rv CGCTTGCAACGCAGCA |

TABLE 2-continued

| Primer | species | SEQ ID NO | Sequence |
|---|---|---|---|
| PER2 | human | 19 | Fw CCACGAGAATGAAATCCGCT |
|  |  | 20 | Rv CCCGCACCTTGACCAGG |

REFERENCES

Albrecht, U., 2013. Circadian Clocks and Mood-Related Behaviors. In A. Kramer & M. Merrow, eds. *Circadian Clocks, Handbook of Experimental Pharmacology*. Handbook of Experimental Pharmacology. Berlin, Heidelberg: Springer Berlin Heidelberg, pp. 227-239.

Albrecht, U. & Oster, H., 2001. The circadian clock and behavior. *Behavioural brain research*, 125(1-2), pp. 89-91.

Brown, S. a et al., 2005. The period length of fibroblast circadian gene expression varies widely among human individuals. *PLoS biology*, 3(10), p.e338.

Harris, A. & Seckl, J., 2011. Glucocorticoids, prenatal stress and the programming of disease. *Hormones and behavior*, 59(3), pp. 279-289.

Hu, K. et al., 2009. Non-random fluctuations and multi-scale dynamics regulation of human activity. *Neuroscience*, 149, pp. 508-517.

Kiessling, S., Eichele, G. & Oster, H., 2010. Adrenal glucocorticoids have a key role in circadian resynchronization in a mouse model of jet lag. *The Journal of clinical investigation*, 120(7), pp. 2600-9.

Ko, C. H. & Takahashi, J. S., 2006. Molecular components of the mammalian circadian clock. *Human molecular genetics*, 15 Spec No, pp.R271-7.

Lavebratt, C. et al., 2010. PER2 variation is associated with depression vulnerability. *Am J Med Genet B Neuropsychiatr Genet*, 153B(2), pp. 570-581.

Leliayski, a. et al., 2014. Adrenal Clocks and the Role of Adrenal Hormones in the Regulation of Circadian Physiology. *Journal of Biological Rhythms*, 30(1), pp. 20-34.

Maccari, S. et al., 2014. The consequences of early life adversity: neurobiological, behavioural and epigenetic adaptations. *Journal of neuroendocrinology*, 26(110), pp. 707-723.

Mairesse, J. et al., 2013. Chronic agomelatine treatment corrects the abnormalities in the circadian rhythm of motor activity and sleep/wake cycle induced by prenatal restraint stress in adult rats. *The international journal of neuropsychopharmacology/official scientific journal of the Collegium Internationale Neuropsychopharmacologicum (CINP)*, 16(2), pp. 323-38.

Marrocco, J. et al., 2014. The effects of antidepressant treatment in prenatally stressed rats support the glutamatergic hypothesis of stress-related disorders. *The Journal of neuroscience: the official journal of the Society for Neuroscience*, 34(6), pp. 2015-24.

Partonen, T. et al., 2007. Three circadian clock genes Per2, Arntl, and Npas2 contribute to winter depression. *Ann Med*, 39(3), pp. 229-238.

Reddy, T. E. et al., 2012. The hypersensitive glucocorticoid response specifically regulates period 1 and expression of circadian genes. *Molecular and cellular biology*, 32(18), pp. 3756-67.

Scott, A., Monk, T. & Brink, L., 1997. Shiftwork as a Risk Factor for Depression: A Pilot Study. *International journal of occupational and environmental health*, 3(Supplement 2), pp.S2-S9.

Tapia-Osorio, A. et al., 2013. Disruption of circadian rhythms due to chronic constant light leads to depressive and anxiety-like behaviors in the rat. *Behavioural brain research*, 252, pp. 1-9.

Welsh, D. K. et al., 2004. Bioluminescence imaging of individual fibroblasts reveals persistent, independently phased circadian rhythms of clock gene expression. *Current biology: CB*, 14(24), pp. 2289-95.

Yoo, S.-H. et al., 2004. PERIOD2::LUCIFERASE real-time reporting of circadian dynamics reveals persistent circadian oscillations in mouse peripheral tissues. *Proceedings of the National Academy of Sciences of the United States of America*, 101(15), pp. 5339-46.

The invention claimed is:

1. A method for assessing a subject's alterations in circadian rhythm, said method comprising measuring the changes in expression of one or more clock gene(s) according to a method for identifying alterations in circadian rhythms in a subject that are reflected in changes in the expression of one or more clock gene(s) in said subject, said method comprising:
   a) obtaining a biological sample from the subject;
   b) isolating fibroblasts from the sample to provide a second sample;
   c) synchronizing the expression of the clock genes in the second sample by means of a first pulse exposure of said second sample to a glucocorticoid;
   d) measuring the expression of clock genes from serial samples from said second sample collected at multiple time points after synchronization; and
analyzing the circadian rhythm parameter(s) (period, amplitude and/or phase) in the series of samples of step (d) and comparing the parameters obtained with circadian rhythm parameters obtained from a control sample to determine a change in the expression of one or more clock gene(s), and
   estimating the intrinsic rhythmicity of spontaneous activity by using an actigraphy device on said subject to obtain behavioral profile data, wherein said behavioral profile data is analysed in combination with results obtained from said measuring the changes in expression of one or more clock gene(s).

2. The method of claim 1, wherein said actigraphy device is worn for about 5-7 days.

3. The method of claim 1, wherein raw activity data from the actigraphy is analysed using one or more of the following algorithms: cosinor analysis, unbiased periodogram analysis, and detrended fluctuation analysis to generate said behavioral profile data.

4. The method of claim 3, the method further comprising:
f) culturing the second sample for a period of time;
g) resetting (phase-shifting) the expression of the clock genes with a second pulse exposure of said second sample to a glucocorticoid;
h) measuring the expression of the same clock genes measured in step (d), in serial samples from said second sample collected at multiple time points; and
i) analyzing a circadian rhythm parameter(s) (period, amplitude and/or phase) of the series of samples of step (h) and comparing the parameters obtained with circadian rhythm parameters from step (d), and/or with circadian rhythm parameters obtained,
wherein results from the actigraphy analysis are analyzed in combination with results obtained from said measuring the changes in expression of one or more clock gene(s) in order to estimate the risk of a subject developing a neuropsychiatric disorder, wherein the subject is identified as being at increased risk of having or developing depression if said measuring of changes in one or more clock gene(s) shows at least one of: decreased amplitude of oscillations in step i) and lack of a phase-shift response in the samples of step h) as compared with the samples of step (d) or the control sample.

5. The method of claim 3, the method further comprising:
f) culturing the second sample for a period of time;
g) resetting (phase-shifting) the expression of the clock genes with a second pulse exposure of said second sample to a glucocorticoid;
h) measuring the expression of the same clock genes measured in step (d), in serial samples from said second sample collected at multiple time points; and
i) analyzing a circadian rhythm parameter(s) (period, amplitude and/or phase) of the series of samples of step (h) and comparing the parameters obtained with circadian rhythm parameters from step (d), and/or with circadian rhythm parameters obtained,
wherein results from the actigraphy analysis are analyzed in combination with results obtained from said measuring the changes in expression of one or more clock gene(s) in order to predict the pharmacoresponse of a subject to a psychotic drug, or guide further treatment of a neuropsychiatric disorder in subject having previously received treatment with said psychotropic drug, wherein the subject is identified as being unresponsive to said psychotropic drug if said measuring of changes in one or more clock gene(s) shows decreased amplitude of oscillations in step i) and/or lack of a phase-shift response in the samples of step h) as compared with the samples of step (d) and/or the control sample.

6. A method for assessing a subject's alterations in circadian rhythm, said method comprising:
a) measuring the changes in expression of one or more clock gene(s) according to a method for identifying alterations in circadian rhythms in a subject that are reflected in changes in the expression of one or more clock gene(s) in said subject, said method comprising:
a') obtaining a biological sample from the subject;
b') isolating fibroblasts from the sample to provide a second sample;
c') synchronizing the expression of the clock genes in the second sample by means of a first pulse exposure of said second sample to a glucocorticoid;
d') measuring the expression of clock genes from serial samples from said second sample collected at multiple time points after synchronization and;
analyzing the circadian rhythm parameter(s) (period, amplitude and/or phase) in the series of samples of step (d') and comparing the parameters obtained with circadian rhythm parameters obtained from a control sample to determine a change in the expression of one or more clock gene(s); and
b) estimating the circadian entrainment of said subject by using an actigraphy device on said subject to generate activity data recordings and analyzing the activity data recordings to generate a behavioral profile for said subject,
wherein the behavioral profile obtained in step b) is analyzed in combination with results obtained from said measuring the changes in expression of one or more clock gene(s).

7. The method of claim 6, wherein step b) comprises using one or more of the following algorithms: cosinor analysis, unbiased periodogram analysis, and detrended fluctuation analysis.

8. A method for assessing a subject's alterations in circadian rhythm, said method comprising:
a) measuring the changes in expression of one or more clock gene(s) according to a method for identifying alterations in circadian rhythms in a subject that are reflected in changes in the expression of one or more clock gene(s) in said subject, said method comprising:
a') obtaining a biological sample from the subject;
b') isolating fibroblasts from the sample to provide a second sample;
c') synchronizing the expression of the clock genes in the second sample by means of a first pulse exposure of said second sample to a glucocorticoid;
d') measuring the expression of clock genes from serial samples from said second sample collected at multiple time points after synchronization and;
analyzing the circadian rhythm parameter(s) (period, amplitude and/or phase) in the series of samples of step (d') and comparing the parameters obtained with circadian rhythm parameters obtained from a control sample to determine a change in the expression of one or more clock gene(s);
b) recording activity using an actigraphy device on said subject;
c) analyzing activity data obtained in step b) to assess an alteration in circadian entrainment of said subject, wherein said alteration is one or more of: a non-preserved period, a non-preserved phase and a non-preserved amplitude; and
d) combining results from steps a) and c).

9. The method of claim 8, wherein step c) uses one or more of the following algorithms: cosinor analysis, unbiased periodogram analysis, and detrended fluctuation analysis.

* * * * *

SEQUENCE LISTING

```
<160> NUMBER OF SEQ ID NOS: 20

<210> SEQ ID NO 1
<211> LENGTH: 19
<212> TYPE: DNA
<213> ORGANISM: Artificial Sequence
<220> FEATURE:
<223> OTHER INFORMATION: Mouse

<400> SEQUENCE: 1
caaggccgag aatgggaag                                                  19

<210> SEQ ID NO 2
<211> LENGTH: 20
<212> TYPE: DNA
<213> ORGANISM: Artificial Sequence
<220> FEATURE:
<223> OTHER INFORMATION: Mouse

<400> SEQUENCE: 2
ggcctcaccc catttgatgt                                                 20

<210> SEQ ID NO 3
```

<210> SEQ ID NO 3
<211> LENGTH: 21
<212> TYPE: DNA
<213> ORGANISM: Artificial Sequence
<220> FEATURE:
<223> OTHER INFORMATION: Mouse

<400> SEQUENCE: 3
ggcgttgttg attggactag g                                    21

<210> SEQ ID NO 4
<211> LENGTH: 21
<212> TYPE: DNA
<213> ORGANISM: Artificial Sequence
<220> FEATURE:
<223> OTHER INFORMATION: Mouse

<400> SEQUENCE: 4
gaatggagtc tccaacaccc a                                    21

<210> SEQ ID NO 5
<211> LENGTH: 20
<212> TYPE: DNA
<213> ORGANISM: Artificial Sequence
<220> FEATURE:
<223> OTHER INFORMATION: Mouse

<400> SEQUENCE: 5
aaccttcccg cagctaacag                                      20

<210> SEQ ID NO 6
<211> LENGTH: 20
<212> TYPE: DNA
<213> ORGANISM: Artificial Sequence
<220> FEATURE:
<223> OTHER INFORMATION: Mouse

<400> SEQUENCE: 6
agtcctcttt gggccacctt                                      20

<210> SEQ ID NO 7
<211> LENGTH: 23
<212> TYPE: DNA
<213> ORGANISM: Artificial Sequence
<220> FEATURE:
<223> OTHER INFORMATION: Mouse

<400> SEQUENCE: 7
ccagattggt ggaggttact gag                                  23

<210> SEQ ID NO 8
<211> LENGTH: 23
<212> TYPE: DNA
<213> ORGANISM: Artificial Sequence
<220> FEATURE:
<223> OTHER INFORMATION: Mouse

<400> SEQUENCE: 8
gcgagagtct tcttggagca gta                                  23

<210> SEQ ID NO 9
<211> LENGTH: 21
<212> TYPE: DNA
<213> ORGANISM: Artificial Sequence
<220> FEATURE:
<223> OTHER INFORMATION: Mouse

<400> SEQUENCE: 9

```
agaacgcgga tatgtttgct g                                          21

<210> SEQ ID NO 10
<211> LENGTH: 21
<212> TYPE: DNA
<213> ORGANISM: Artificial Sequence
<220> FEATURE:
<223> OTHER INFORMATION: Mouse

<400> SEQUENCE: 10
atctaagccg ctgcacacac t                                          21

<210> SEQ ID NO 11
<211> LENGTH: 19
<212> TYPE: DNA
<213> ORGANISM: Artificial Sequence
<220> FEATURE:
<223> OTHER INFORMATION: Mouse

<400> SEQUENCE: 11
ggaacggacc gtcacctttt                                            19

<210> SEQ ID NO 12
<211> LENGTH: 19
<212> TYPE: DNA
<213> ORGANISM: Artificial Sequence
<220> FEATURE:
<223> OTHER INFORMATION: Mouse

<400> SEQUENCE: 12
tccnctgctc ccattgagt                                             19

<210> SEQ ID NO 13
<211> LENGTH: 20
<212> TYPE: DNA
<213> ORGANISM: Artificial Sequence
<220> FEATURE:
<223> OTHER INFORMATION: Human

<400> SEQUENCE: 13
accccacgaa gtgttggata                                            20

<210> SEQ ID NO 14
<211> LENGTH: 20
<212> TYPE: DNA
<213> ORGANISM: Artificial Sequence
<220> FEATURE:
<223> OTHER INFORMATION: Human

<400> SEQUENCE: 14
aagcagatgg ccacagaact                                            20

<210> SEQ ID NO 15
<211> LENGTH: 20
<212> TYPE: DNA
<213> ORGANISM: Artificial Sequence
<220> FEATURE:
<223> OTHER INFORMATION: Human

<400> SEQUENCE: 15
gccgaatgat tgctgaggaa                                            20

<210> SEQ ID NO 16
<211> LENGTH: 20
<212> TYPE: DNA
```

```
<213> ORGANISM: Artificial Sequence
<220> FEATURE:
<223> OTHER INFORMATION: Human

<400> SEQUENCE: 16
gggaggcgta ctcgtgatgt                                           20

<210> SEQ ID NO 17
<211> LENGTH: 24
<212> TYPE: DNA
<213> ORGANISM: Artificial Sequence
<220> FEATURE:
<223> OTHER INFORMATION: Human

<400> SEQUENCE: 17
tctacatttc ggagcaggca gccg                                      24

<210> SEQ ID NO 18
<211> LENGTH: 16
<212> TYPE: DNA
<213> ORGANISM: Artificial Sequence
<220> FEATURE:
<223> OTHER INFORMATION: Human

<400> SEQUENCE: 18
cgcttgcaac gcagca                                               16

<210> SEQ ID NO 19
<211> LENGTH: 20
<212> TYPE: DNA
<213> ORGANISM: Artificial Sequence
<220> FEATURE:
<223> OTHER INFORMATION: Human

<400> SEQUENCE: 19
ccacgagaat gaaatccgct                                           20

<210> SEQ ID NO 20
<211> LENGTH: 17
<212> TYPE: DNA
<213> ORGANISM: Artificial Sequence
<220> FEATURE:
<223> OTHER INFORMATION: Human

<400> SEQUENCE: 20
cccgcacctt gaccagg                                              17
```